(12) United States Patent
Schiess et al.

(10) Patent No.: US 11,320,435 B2
(45) Date of Patent: May 3, 2022

(54) METHOD OF DETECTING PROTEINS IN HUMAN SAMPLES AND USES OF SUCH METHODS

(71) Applicant: ProteoMedix AG, Schlieren (CH)

(72) Inventors: Ralph Schiess, Zürich (CH); Kathrin Endt, Germering (DE); Alcibiade Athanasiou, Baden (CH); Annalisa Macagno, Schlieren (CH); Thomas Steuber, Hamburg (DE)

(73) Assignee: ProteoMedix AG, Schlieren (CH)

( * ) Notice: Subject to any disclaimer, the term of this patent is extended or adjusted under 35 U.S.C. 154(b) by 377 days.

(21) Appl. No.: 16/318,012

(22) PCT Filed: Jul. 11, 2017

(86) PCT No.: PCT/EP2017/067411
§ 371 (c)(1),
(2) Date: Jan. 15, 2019

(87) PCT Pub. No.: WO2018/011212
PCT Pub. Date: Jan. 18, 2018

(65) Prior Publication Data
US 2019/0250163 A1    Aug. 15, 2019

(30) Foreign Application Priority Data
Jul. 15, 2016 (EP) ..................... 16179607

(51) Int. Cl.
*G01N 33/574* (2006.01)

(52) U.S. Cl.
CPC . *G01N 33/57434* (2013.01); *G01N 33/57488* (2013.01); *G01N 2333/96433* (2013.01); *G01N 2400/00* (2013.01)

(58) Field of Classification Search
CPC ....... G01N 33/57434; G01N 33/57488; G01N 2333/96433; G01N 2400/00
See application file for complete search history.

(56) References Cited

U.S. PATENT DOCUMENTS 10,151,755 B2 * 12/2018 Krek ................ G01N 33/57407
2011/0065605 A1 * 3/2011 Krek ................ G01N 33/57434
506/9

FOREIGN PATENT DOCUMENTS

| WO | 96/26441 A1 | 8/1996 |
| WO | 2009/138392 A1 | 11/2009 |

OTHER PUBLICATIONS

Brawer, Prostate-specific antigen: current status, CA Cancer J Clin, 1999, 49:264-281. (Year: 1999).*
Basso et al., Total PSA, Free PSA/Total PSA Ratio, and Molecular PSA Detection in Prostate Cancer: Which is Clinically Effective and When? Urology 55(5):710-715, Publication Year: 2000 (Year: 2000).*
Etzioni et al., The case for early detection, Nature Review, 2003, 3: 1-10, Publication Date: Apr. 2003 (Year: 2003).*
THBS1 gene card: https://www.genecards.org/cgi-bin/carddisp.pl?gene=THBS1 (Year: 2021).*
Landers et al. Use of multiple biomarkers for a molecular diagnosis of prostate cancer, Int. J. Cancer 114, 950-956, Publication Date: Dec. 17, 2004 (Year: 2004).*
Bagley et al., Logistic regression in the medical literature: Standards for use and reporting, with particular attention to one medical domain, Journal of Clinical Epidemiology, 54, 979-985, Publication Date: Sep. 21, 2001 (Year: 2001).*
Thermo, ELISA technical guide and protocols, https://assets.fishersci.com/TFS-Assets/LSG/Application-Notes/TR0065-ELISA-guide.pdf, Publication Year: 2010 (Year: 2010).*
Thakur et al, Revisiting the dilution factor as vital parameter for sensitivity of ELISA assay in CSF and Plasma, Annals of Neurosciences, 22(1), 37-42, Publication Date: Jan. 2015 (Year: 2015).*
Vital et al., The Senescence-Associated Secretory Phenotype Promotes Benign Prostatic Hyperplasia, The American Journal of Pathology, 184, 3, 721-731, Publication Date: Mar. 2014 (Year: 2014).*
Zhang et al., Predicting detection limits of enzyme-linked immunosorbent assay (ELISA) and bioanalytical techniques in general, Analyst, 139,439-445, Publication year: 2014 (Year: 2014).*
Clemmensen et al. Plasma levels of OLFM4 in normals and patients with gastrointestinal cancer, J. Cell. Mol. Med. 19, 12, 2865-2873, Publication Year: 2015 (Year: 2015).*
Stoltzfus JC, Logistic Regression: A Brief Primer, Academic Emergency Medicine, 18, 1099-1104, Publication Year: 2011 (Year: 2011).*
ICAM-1 ELISA Kit, User Guide, Invitrogen, https://assets.thermofisher.com/TFSAssets/LSG/manuals/MAN0016468_201_Hu_sICAM-1_ELISA_UG.pdf (Year: 2020).*
Human Cathepsin D Elisa Kit (ab119586) Product Overview, Abeam, https://www.abcam.com/human-cathepsin-d-elisa-kit-ab119586.html (Year: 2021).*
Klaus JUNG et al., "Ratio of Free or Complexed Prostate-specific Antigen (PSA) to Total PSA: Which Ratio Improves Differentiation between Benign Prostatic Hyperplasia and Prostate Cancer?" Clinical Chemistry, 2000, pp. 55-62. vol. 46, No. 1.
Brian M. Nolen et al., "An extensive targeted proteomic analysis of disease-related protein biomarkers in urine from healthy donors", PLOS ONE, Jan. 1, 2013, 11 pgs., vol. 8, No. 5.
Michael W. Shafer et al., "Antibody Array Profiling Reveals SerumTSP-l as a Marker to Distinguish Benign From Malignant Prostatic Disease", The Prostate, 2007, pp. 255-267, vol. 67.

(Continued)

*Primary Examiner* — Peter J Reddig
*Assistant Examiner* — Cheng Lu
(74) *Attorney, Agent, or Firm* — Sughrue Mion, PLLC

(57) ABSTRACT

A method for collecting information about the health status of a subject is proposed involving the quantitative detection, in serum, plasma or blood of the subject, of the concentration of THBS1, the proportion of free PSA (% fPSA), preferably including the concentration of at least one protein selected from the group consisting of CTSD, OLFM4, ICAM1.

19 Claims, 7 Drawing Sheets

(56) References Cited

OTHER PUBLICATIONS

International Search Report for PCT/EP2017/067411 dated, Oct. 4, 2017 (PCT/ISA/210).
Written Opinion of the International for PCT/EP2017/067411 dated Oct. 4, 2017 (PCT/ISA/237).
Baker, H., et al., "Conversion of a Capture ELISA to a Luminex xMAP Assay using a Multiplex Antibody Screening Method", Journal of Visualized Experiments and Luminex Corporation. vol. 65, e4084, Jul. 2012, pp. 1-8.
Emanuelsson, O., et al., "Locating proteins in the cell using TargetP, SignalP and related tools", Nature Protocols, vol. 2, No. 4, 2007, pp. 953-971 (19 pages).

* cited by examiner

METHOD OF DETECTING PROTEINS IN HUMAN SAMPLES AND USES OF SUCH METHODS

CROSS REFERENCE TO RELATED APPLICATIONS

This application is a National Stage of International Application No. PCT/EP2017/067411 filed Jul. 11, 2017, claiming priority based on European Patent Application No. 16179607.3, filed Jul. 15, 2016.

TECHNICAL FIELD

The present invention relates to the field of methods for the measurement of proteins in human samples, in particular in human serum, plasma or blood, and it also relates to assays and uses of such assays, in particular for risk assessment.

PRIOR ART

The measurement of proteins in human samples of a person is a powerful tool for the supervision and the risk assessment of the general status of the person, in particular as concerns the nutritional and health status of the person.

Prostate cancer (PCa) is the most frequently diagnosed cancer in men and the second leading cause of male cancer related deaths in the US.

The diagnosis and treatment of prostate cancer, despite decennial research efforts, are still a major challenge in the clinics. PCa progression is unfortunately silent, and an early detection of faster progressing and potentially dangerous lesions is crucial for the patient's health, since complete remission and cure from the disease is possible only at early stages of the disease.

The best noninvasive diagnostic test available for PCa is the detection of the Prostate Specific Antigen (PSA) in the blood coupled with digital rectal examination (DRE). PSA is a protein produced by the epithelial cells of the prostate gland. PSA is also known as kallikrein III, seminin, semenogelase, γ-seminoprotein and P-30 antigen and it is a 34 kD glycoprotein present in small quantities in the serum of normal men, and is often elevated in the presence of PCa and in other prostate disorders. A blood test to measure PSA coupled with DRE is the most effective test currently available for the early detection of PCa. Higher-than-normal levels of PSA are associated with both localized and metastatic PCa.

The diagnostic accuracy of PSA alone is only around 60% and the methodology has major drawbacks in specificity (too many false positives cases that undergo unneeded prostate biopsy or surgery). Indeed PSA levels can be also increased by prostate infection, irritation, benign prostatic hypertrophy (enlargement) or hyperplasia (BPH), and recent ejaculation, producing a false positive result.

Thus, PCa diagnosis is currently hampered by the high false-positive rate of PSA evaluations, which consequently may lead to a high number of prostate biopsies with negative diagnostic findings. Further, these unnecessary biopsies can have potential side effects. Recent recommendations against widespread screening of men for PCa using PSA have resulted in fewer men being screened for PCa, and fewer early-stage cases being detected.

A reliable and non-invasive diagnostic/prognostic procedure that is avoiding false positive and false negative results is thus still lacking, even though novel methodologies based on the simultaneous measurement of various parameters (e.g. free and total PSA) are emerging as tools to increase the overall diagnostic accuracy. Most PSA in the blood is bound to serum proteins. A small amount is not protein bound and is called free PSA. In men with prostate cancer the ratio of free (unbound) PSA to total PSA is decreased. The risk of cancer increases if the ratio of free to total PSA (% fPSA) is less than 25%. The lower the ratio, the greater the probability of PCa. However, both total and free PSA increase immediately after ejaculation, returning slowly to baseline levels within 24 hours, and also other mechanisms not related to PCa can influence the free to total PSA ratio. New diagnostic tools, ideally non-invasive ones, are urgently needed to improve PCa diagnosis and reduce unnecessary biopsies and overtreatment. More accurate diagnostics from easily accessible sample types like blood will allow physicians and patients to make more informed decisions about potential cases of PCa and whether a prostate biopsy is required.

Similar to diagnosis, treatment and/or prognosis of PCa remains a major challenge due to heterogeneity of the disease. Although multiple mechanisms of PCa have been suggested, the lack of suitable signatures able to stratify patients and key target proteins for therapeutic intervention cures are still not within reach.

One approach to find a suitable diagnostic system for prostate cancer is proposed in WO 2009/138392, where it is proposed to measure at least two of a list of 24 proteins known to be present in human blood, and expected to be down regulated or upregulated depending on the health status of the corresponding patient.

The problem with known approaches is that they still suffer a lack of sensitivity and in particular specificity in terms of which cancer is actually present, and a lack of diagnostic reliability in terms of avoiding false positive and false negative results. A further problem is the actual availability of corresponding detection probes, be it antibody-based or any other type of detection, making the corresponding tools suitable not only for academic purposes but also for broad applications. A further issue is that the corresponding detection systems should be simple and not entail a large number of individual measurements.

SUMMARY OF THE INVENTION

It is therefore an object of the present invention to propose a new method for collecting information about the health status of a subject in particular for the detection of proteins in human samples, in particular in human serum, plasma or blood, and it also relates to assays and uses of such assays, in particular for risk assessment, in particular in relation to PCa. Four individual immunoassays for human cathepsin D (CTSD), human intercellular adhesion molecule 1 (ICAM1), human olfactomedin 4 (OLFM4), and human thrombospondin 1 (THBS1) were developed and technically validated. The mouse homologues of these glycoproteins were previously identified by mass spectrometry using a Pten conditional knock-out mouse model. The human homologues were measured in clinical serum samples for testing the capability of discriminating benign prostatic conditions from PCa either by themselves or in combination with PSA values, in particular % fPSA values. As a result, it was identified that the claimed combination is the optimum to overcome the above-mentioned defects of prior art approaches.

More specifically, the present invention relates to a method for collecting information about the health status of a subject. The method involves the quantitative detection of specific proteins in serum, blood, or plasma of the subject. The serum, blood, or plasma of the subject can also be stored and/or pretreated, e.g. diluted, after having been taken from the subject and before carrying out the method. Specifically, the method involves the measurement of the concentration of THBS1, as well as the measurement/determination of the proportion of free PSA (% fPSA, given as [free PSA]/[total PSA] and thus being in the numerical range of 0-1). Preferably it further involves the measurement of the concentration of at least one protein selected from the group consisting of CTSD, OLFM4, ICAM1. In other words at least 2 or preferably at least 3 protein contents are measured/determined in the sample for collecting information. For THBS1, CTSD, OLFM4 and/or ICAM1 the concentration is directly or indirectly determined, typically expressed in ng/ml, while for the PSA the proportion of free PSA is determined by quantifying the concentration of total and free PSA (or alternatively by quantifying the concentration of total and complexed PSA and calculating the proportion of free PSA therefrom), and used for the analysis. For the analysis preferably the concentration values in the original sample, so in the original serum, blood or plasma, are used, and if there is a step of dilution or modification of the original serum, blood or plasma prior to measurement, the concentration in the original sample is back calculated.

Unexpectedly, it was found that the concentration of THBS1, in combination with the proportion of free PSA (% fPSA) is highly indicative of a positive prostate biopsy and thus PCa. Unexpectedly, it was found that THBS1 not in the combination with the total PSA but specifically in the combination with the % fPSA value allows for the determination of a positive information about the health status of the corresponding subject. The analysis carried out on a large cohort shows that with an optimized logistic regression model a parameterization can be found with a very large area under the curve (AUC) in the receiver operating characteristic (ROC) representation and with a particularly high specificity at 90% sensitivity. In addition to that, it was found that any of the additional systems CTSD, OLFM4, ICAM1 if evaluated and optimized alone and again together with the proportion of % fPSA on this cohort, no large AUC can be obtained. However, in particular if one further of the group CTSD, OLFM4, ICAM1 is measured, in particular if CTSD is measured together with THBS1 and in conjunction with % fPSA a significant additional specificity at 90% sensitivity can be obtained.

It is also possible to further include information such as about the age of the corresponding patient into the analysis, such additional information such as the age can also be used as a further parameter in the formula (1) given below.

Typically the method is carried out on subjects having elevated PSA (2.0 and 10 ng/ml) values, preferably further having negative DRE and/or enlarged prostates (≥35 ml).

According to a first preferred embodiment of the proposed method, the method includes: a first step being performed by contacting the subject's serum, plasma or blood, preferably serum, preferably after dilution thereof, with at least one, preferably two (preferably using a sandwich approach) affinity reagent(s) for each protein and detecting whether binding occurs between the respective protein and the at least one (or two) affinity reagent(s) and using quantitative readout of the respective protein's concentration or in case of free PSA its proportion % fPSA value, allowing the calculation of the respective concentration in the original serum, plasma or blood; a second step of calculating, based on all the protein concentrations as well as the free PSA proportion determined in the first step, a combined score value.

The protein concentrations as well as the free PSA proportion are typically individually measured, e.g. each in an immunoassay, but then the determined concentrations/proportions are used in a combined manner for the calculation of the combined score value. So the measured information is not used individually but is used in a combined manner for the determination of the combined score value and for further analysis of the information.

Further preferably, after the second step, in a third step the risk of having a positive prostate biopsy and thus PCa of the subject can be determined based on the combined score value as determined in the second step, wherein surpassing a corresponding threshold value of the combined score value is taken as a prediction of a positive biopsy (meaning extraction of sample tissue for examination to determine the presence or extent of a disease, wherein the tissue is examined under a microscope by e.g. a pathologist, and positive means that the person examining draws the conclusion that there is cancer) and therefore as positive PCa information that necessitates confirmatory biopsy.

The combined score value is preferably calculated using the following formula:

$$\frac{1}{1+e^{-(\beta_0+\beta_1\cdot x_1+\cdots+\beta_k\cdot x_k)}} \qquad (1)$$

wherein $\beta_i$ are the regression coefficients as determined beforehand with an optimization, typically a maximization of the AUC in a ROC approach, using experimental data, $\beta_0$ being the intercept, and wherein $x_i$ is the measured concentration (ng/ml) of the respective protein in the original serum, plasma or blood and in case of % fPSA it is the proportion of free to total PSA (expressed in the range of 0-1) thereof in the original serum, plasma or blood. The index i therefore in the present situation runs from 0 to at least 2, for the situation were only THBS1 and % fPSA values are used, and to at least 3, where further protein concentration values from the above-mentioned group are measured.

If for example THBS1, CTSD and % fPSA are measured for the calculation of the combined score value, i runs up to 3 and $\beta_1$ is $\beta_{CTSD}$, $x_1$ is the concentration of CTSD in the original serum, plasma or blood, $\beta_2$ is $\beta_{THBS1}$, $x_2$ is the concentration of THBS1 in the original serum, plasma or blood, and $\beta_3$ is $\beta_{\%\,fPSA}$, $x_3$ is the proportion of free PSA in the original serum, plasma or blood.

The corresponding optimization of the logistic regression is carried out using measurements on serum, plasma or blood from subjects where one has more detailed information about the health status, and where one knows whether there is a negative or a positive prostate biopsy and thus PCa. This cohort is therefore used for finding an optimum model in the ROC representation and to obtain a maximum AUC, in order to find the highest possible specificity at high sensitivity. The corresponding parameters $\beta_i$ which are the regression coefficients can subsequently be used on any individual where one does not have knowledge about the health status, to make a probability statement about the health status of the subject and thus predict prostate biopsy outcome.

The concentration/proportions of the proteins are measured and inserted into the above-mentioned formula to determine the combined score value. The obtained corresponding combined score value is then compared with a threshold value. The threshold value can be chosen according to the desired sensitivity/specificity. If this threshold value is then exceeded, a positive prostate biopsy and thus PCa diagnosis is given together with the proposal to go for a biopsy. The corresponding threshold values for a desired sensitivity is determined in that in the ROC representation the corresponding point on the curve where there is the desired sensitivity is selected, and the combined score value is taken for that point. The threshold values given below for the specific parameterizations are always given for 90% sensitivity. If the given threshold values are exceeded this is indicative of a high likelihood of a prostate biopsy and thus PCa, suggesting biopsy to find out in detail. Using a large cohort on 474 serum samples of patients undergoing prostate biopsy the following preferred parameterizations were determined for optimum sensitivity and specificity, wherein the concentration of the proteins, i.e. THBS1, CTSD, ICAM1 and OLFM4, respectively, is in each case to be inserted into the formula as ng/ml and as determined/back-calculated for the original blood, serum, or plasma, and wherein the proportion of the free PSA (% fPSA) is to be used as a number in the range of 0-1:

For the case, where the concentration of THBS1, as well as the proportion of free PSA (% fPSA) is measured in the first step, preferably for the calculation of the combined score value the regression coefficients are chosen as follows:

$\beta_0$ in the range of 4.0-5.5 or 4.5-5.0, preferably in the range of 4.5-5.0 or 4.7-4.8;

$\beta_{THBS1}$ in the range of (−0.00012)-(−0.00003) or (−0.00009)-(−0.00003), preferably in the range of (−0.00009)-(−0.00004) or (−0.00006)-(−0.00004);

$\beta_{\%\,fPSA}$ in the range of (−7.5)-(−2.5), preferably in the range of (−5.5)-(−5.0).

For a 90% sensitivity in this case preferably a threshold value of the combined score value of 0.28-0.35, preferably 0.30-0.34 or 0.30-0.33 is selected.

For the case, where the concentration of THBS1, the proportion of free PSA (% fPSA), as well as the concentration of CTSD is measured in the first step, preferably for the calculation of the combined score value the regression coefficients are chosen as follows:

$\beta_0$ in the range of 3-4.2 or 3-3.4, preferably in the range of 3.8-4.0 or 3.1-3.3;

$\beta_{CTSD}$ in the range of 0.003-0.05 or 0.005-0.05, preferably in the range of 0.004-0.006 or 0.008-0.012;

$\beta_{THBS}1$ in the range of (−0.0002)-(−0.00005) or (−0.00009)-(−0.00003), preferably in the range of (−0.00012)-(−0.00008) or (−0.00007)-(−0.00006);

$\beta_{\%\,fpsA}$ in the range of (−7.5)-(−2.5), preferably in the range of (−5.2)-(−5.0) or (−5.2)-(−4.5). For a 90% sensitivity in this case preferably a threshold value of the combined score value of 0.28-0.40 or 0.28-0.35, preferably 0.35-0.37 or 0.33-0.34 is selected.

For the case, where the concentration of THBS1, the proportion of free PSA (% fPSA), as well as the concentration of OLFM4 is measured in the first step, preferably for the calculation of the combined score value the regression coefficients are chosen as follows:

$\beta_0$ in the range of 4.0-5.2, preferably in the range of 4.4-4.8;

$\beta_{OLFM4}$ in the range of 0.001-0.01, preferably in the range of 0.002-0.004;

$\beta_{THBS1}$ in the range of (−0.00009)-(−0.00002), preferably in the range of (−0.00006)-(−0.00004);

$\beta_{\%\,fPSA}$ in the range of (−7.5)-(−2.5), preferably in the range of (−5.9)-(−4.8).

For a 90% sensitivity in this case preferably a threshold value of the combined score value of 0.27-0.35, preferably 0.3-0.34 is selected, For the case, where the concentration of THBS1, the proportion of free PSA (% fPSA), as well as the concentration of ICAM1 is measured in the first step, preferably for the calculation of the combined score value the regression coefficients are chosen as follows:

$\beta_0$ in the range of 4.0-5.2, preferably in the range of 4.6-4.9;

$\beta_{ICAM1}$ in the range of (−0.002)-(−0.0001), preferably in the range of (−0.0010)-(−0.0005);

$\beta_{THBS1}$ in the range of (−0.0001)-(−0.00001), preferably in the range of (−0.00008)-(−0.00004);

$\beta_{\%\,fPSA}$ in the range of (−7.5)-(−2.5), preferably in the range of (−5.8)-(−4.9).

For a 90% sensitivity in this case preferably a threshold value of the combined score value of 0.25-0.35, preferably 0.3-0.33 is selected.

For the case, the concentration of THBS1, the proportion of free PSA (% fPSA), as well as the concentration of OLFM4, ICAM1 as well as CTSD are measured in the first step, for the calculation of the combined score value the regression coefficients are chosen as follows:

$\beta_0$ in the range of 3-3.8, preferably in the range of 3.5-3.6;

$\beta_{OLFM4}$ in the range of 0.001-0.003, preferably in the range of 0.0015-0.0025;

$\beta_{ICAM1}$ in the range of (−0.004)-(−0.002), preferably in the range of (−0.0035)-(−0.00025);

$\beta_{CTSD}$ in the range of 0.005-0.05, preferably in the range of 0.008-0.012;

$\beta_{THBS1}$ in the range of (−0.00009)-(−0.00003), preferably in the range of (−0.00007)-(−0.00006);

$\beta\%$ fPSA in the range of (−7.5)-(−2.5), preferably in the range of (−5.2)-(−4.8).

For a 90% sensitivity in this case preferably a threshold value of the combined score value of 0.3-0.35, preferably 0.32-0.335 is selected.

The THBS1 and/or at least one of CTSD, OLFM4, ICAM1 as measured may comprise post-translational modifications, including glycosylation, phosphorylation, lipidation etc. For the measurement of the concentration of at least one of THBS1, CTSD, OLFM4, ICAM1 the subject's serum, plasma or blood can be and preferably normally is diluted using a buffer.

This buffer preferably has a pH value in the range of 7-7.4 and preferably further comprises an agent controlling the pH value. This agent controlling the pH value can be selected from at least one of the following systems: Tris (Tris (hydroxymethyl)-aminomethane), Pipes (Piperazine-1,4-bis-2-ethane sulfonic acid), Mes (4-Morpholino ethane sulfonic acid), Hepes (4-(2-hydroxyethyl)-1-piperazine-ethane sulfonic acid), phosphate buffered saline (PBS).

Further the buffer may comprise additional components. For example the buffer may comprise at least one non-ionic detergent, preferably in a concentration of 0.01 to 0.1% (v/v), preferably 0.025-0.05% (v/v). This non-ionic detergent may be selected from at least one the group consisting of: Dodecylpoly(ethyleneglycolether)m, wherein m is an integer of 5 to 40; 1-O-n-Octyl-β-D-glucopyranoside (n-Octylglucoside); Alkylphenolpoly(ethyleneglycol-ether)m, wherein m is an integer of 5 to 40, preferably m=11; 1-O-n-Dodecyl-β-D-glucopyranosyl (1-4)alpha-D-glucopyranoside; Dodecylpoly-(ethyleneglycolether)m, wherein m is an integer of 5 to 40, preferably m=23; Poly(oxyethylene)

(20)-sorbitane mono fatty acid ester, preferably selected from Poly(oxyethylene)(20)-sorbitane monooleate, Poly(oxyethylene)(20)-sorbitane monolaurate, Poly(oxyethylene)(20)-sorbitane monopalmitat, Poly(oxyethylene)(20)-sorbitane monostearate); Octylphenolpoly(ethyleneglycoiether)m, wherein m is an integer of 5 to 40, preferably m=10.

Further the buffer may comprise components such as at least one of bovine serum albumin, trehalose, sucrose, fetal bovine serum, horse serum, mouse IgG, bovine gamma globulin. Preferably the buffer is free from dithiothreitol (DTT) or any other reduction agent, for the case of certain proteins however DTT may also specifically be added (see remarks below). Preferably the buffer has a ionic strength in the range of 50-850 mM, preferably in the range of 200-400 mM or in the range of 250-370 mM.

For the dilution to measure THBS1 a dilution factor in the range of 1:1,000-1:20,000 can be chosen, preferably in the range of 1:1,000-1:3,000 or 1:2,000-1:3,000 for an enzyme linked immunosorbent assay (ELISA) and in the range of 1:5,000-1:15,000 for a bead-based assay.

For the dilution to measure the protein CTSD a dilution factor in the range of 1:5-1:70 or 1:5-1:30 can be chosen, preferably in the range of 1:10-1:50 or 1:10-1:30 for an enzyme linked immunosorbent assay and in the range of 1:10-1:20 for a bead-based assay. Preferably the buffer used and as described above is further and additionally and specifically supplemented with a non-ionic detergent, preferably selected as Poly(oxyethylene)(20)-sorbitane monolaurate to lead to an additional concentration thereof of 0.05% (v/v), For the dilution to measure ICAM1 a dilution factor in the range of 1:50-1:200 can be chosen, preferably in the range of 1:80-1:150. Preferably the buffer used is further supplemented with sodium chloride to an additional sodium chloride content of 250 mM to increase the ionic strength, For the dilution to measure OLFM4 a dilution factor in the range of 1:5-1:30 can be chosen, preferably in the range of 1:5-1:20. Preferably the buffer used is further supplemented with sodium chloride to an additional sodium chloride content of 250 mM as well as a reduction agent, preferably selected as dithiothreitol (DTT) to lead to a concentration of 5 mM thereof.

According to yet another preferred embodiment, the method includes a first step being performed by contacting the subject's serum, plasma or blood, preferably after dilution thereof, with at least one, preferably in a sandwich two, affinity reagent(s) for each protein and detecting whether binding occurs between the respective protein and the at least one (or two) affinity reagent(s) and using quantitative readout of the respective protein's concentration or in case of free PSA its proportion, allowing the calculation of the respective concentration/proportion in the original serum, plasma or blood, and wherein in this step either a sandwich ELISA specific to the respective protein preferably with visible readout is used, and/or a sandwich bead based antibody assay to the respective protein preferably with fluorescent readout.

The sandwich ELISA specific to the respective protein preferably with visible readout and/or the sandwich bead based antibody assay to the respective protein preferably with fluorescent readout can be one obtained by using recombinant proteins of human THBS1, CTSD, ICAM1 and OLFM4, respectively and mouse monoclonal antibodies generated through immunization of mice therewith.

According to yet another preferred embodiment, the quantitative detection of the respective concentration involves the determination of the concentration of such biomarkers relative to an external protein standard, involving the preparation of a reference standard curve by measuring defined concentrations of several, preferably 5-7, protein standards with known concentrations diluted in the same buffer as for the protein dilution to be measured in the same set of measurements of the samples.

The method may further involve a step of or be used in relation with at least one of monitoring, diagnosis, prognosis, risk assessment, therapy selection, therapy monitoring of cancer, in particular prostate cancer, including localized prostate cancer.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
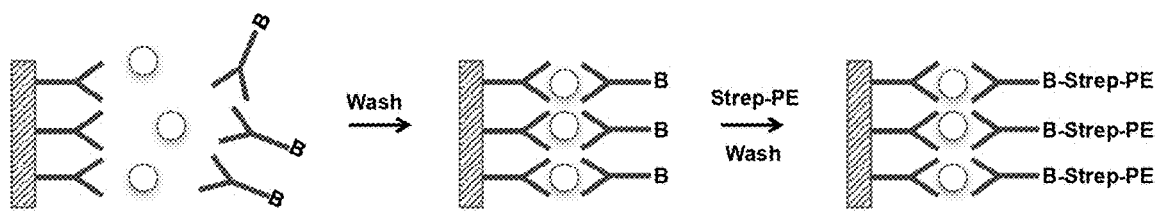
FIG. 1 shows a schematic presentation of a two-step sandwich immunoassay, wherein for the Luminex system the detection is realized using fluorescence with fluorescent Streptavidin-phycoerythrin conjugate (Strep-PE) attaching to the Biotin (B) of the detection antibody, while for ELISA this is realized using color change in the visible range obtained with Streptavidin-enzyme conjugation and a chromogenic substrate for such enzyme, preferably Streptavidin-horseradish peroxidase (HRP) conjugate instead of Strep-PE and the HRP chromogenic substrate TMB.
Figure 2:
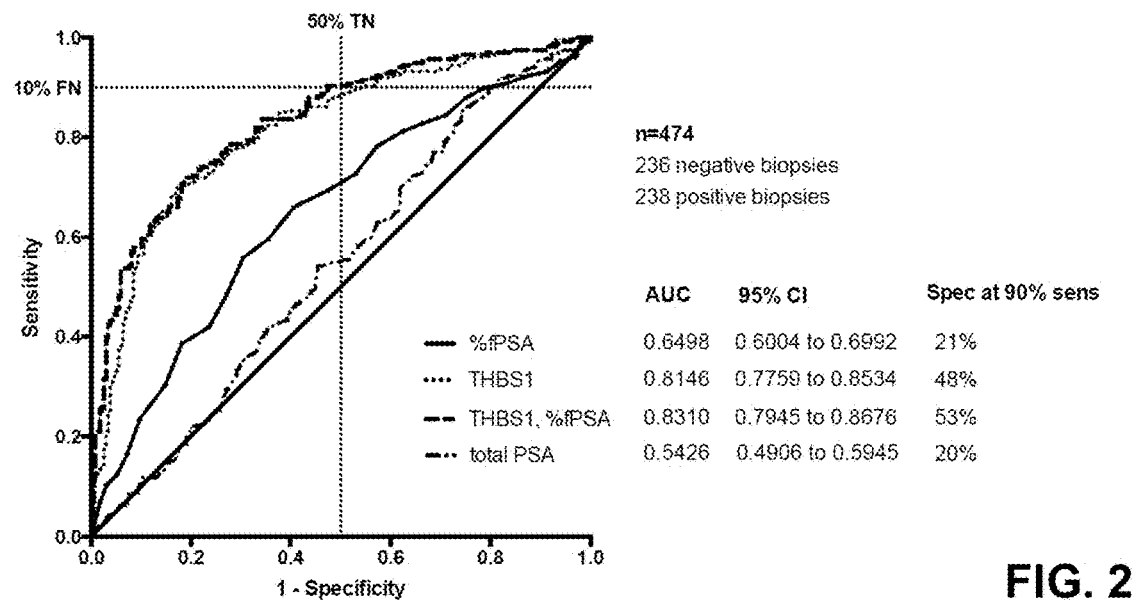
FIG. 2 shows the optimized receiver operating characteristic (ROC) training curves depicting the accuracy of individual predictors of positive prostate biopsy and thus PCa, for the case when THBS1 is measured alone, when total PSA is measured alone, when % fPSA is measured alone, and when the concentration of THBS1 is used together with the proportion of % fPSA for the evaluation of the combined score value.

We have previously identified numerous protein biomarkers for PCa diagnosis using a two staged genetics-guided discovery approach focusing on the PI3K/PTEN cancer pathway. In the first stage, glycoproteins were identified from sera and prostate tissue of wild-type and Pten-null cancer mouse models. Following prioritization of the proteins, proteomic profiles were identified in the sera of PCa patients and control individuals in a second stage validation step. The objective was to identify and develop and validate highly sensitive and highly specific immunoassays for the individual protein biomarkers. The transition from mass spectrometry to immunoassay technology represents an important step in order to enable high-throughput clinical validation in large sample cohorts. Furthermore, it facilitates clinical application of the test in routine diagnostic laboratories. The microparticle-based Luminex platform was initially chosen due to the improved kinetics resulting from a higher surface area of micro particles when compared to microtiter plates or tubes. In addition, magnetic microparticle-based assays are more amenable to automation than tube- or microtiter plate-based assays and thus widely distributed in random-access immunoassay systems. Finally, the multiplexing capabilities of the Luminex system facilitated the antibody selection process for immunoassay development, specifically for the subsequent development of the more common and simple and more user-friendly ELISAs.

In this section, the identification, the development and technical validation according to the guidelines from the Center for Drug Evaluation and Research (CDER) is described for four individual immunoassays for human cathepsin D (CTSD), human intercellular adhesion molecule 1 (ICAM1), human olfactomedin 4 (OLFM4), and human thrombospondin 1 (THBS1). The mouse homologues of these human glycoproteins were previously identified by mass spectrometry using a Pten conditional knock-out mouse model. The human homologues were measured in clinical serum samples for testing the capability of discriminating benign prostatic conditions from PCa. As a result it was identified that the claimed combination is the optimum to overcome the above-mentioned defects of prior art approaches and which shows the highest sensitivity and highest specificity.

The development yielded several individual immunoassays with inter and intra-variability (CV) <15% and linearity on dilution of the analytes. In serum, ex vivo protein stability (<15% loss of analyte) was achieved for a duration of at least 24 hours at room temperature and 2 days at 4° C.

Materials and Methods

Gene names, Entry names, Protein names (shortened) and Accession numbers as generally used in this specification are as defined according to the UniProt Consortium (www.uniprot.org), which is comprised of the European Bioinformatics Institute (EBI), the Swiss Institute of Bioinformatics (SIB), and the Protein Information Resource (PIR). The annotated or predicted cellular localization is according to Emanuelsson O, Brunak S, von Heijne G, Nielsen H. (2007) Locating proteins in the cell using TargetP, SignalP and related tools. Nat Protoc. 2, 953-71.

| Gene name | Entry name | Protein name | Accession number | annotated or predicted cellular localization |
|---|---|---|---|---|
| THBS1 | TSP1_HUMAN | Thrombospondin 1 | P07996 | secreted |
| OLFM4 | OLFM4_HUMAN | Olfactomedin-4 | Q6UX06 | secreted |
| CTSD | CATD_HUMAN | Cathepsin D | P07339 | lysosomal |
| ICAM1 | ICAM1_HUMAN | Intercellular adhesion molecule 1 | P05362 | plasma membrane |
| KLK3 | KLK3_HUMAN | Prostate-specific antigen (PSA) | P07288 | secreted |

Protein Standard/Calibrator

Expression

Recombinant human CTSD (residues 1-412, followed by 6His tag), ICAM1 (residues 1-480, followed by 8His tag), THBS1 (residues 19 to 1170, preceded by a signal peptide and followed by 11His tag) and OLFM4 (residues 1-510) were each expressed and purified from cell culture supernatants of transfected HEK293 cells. CTSD, ICAM1, THBS1 was purified using a His Trap column (GE Healthcare).

Purification

For ICAM1 ammonium sulfate precipitation was first carried out. Proteins precipitating at 35% were eliminated by centrifugation. The supernatant was transferred to clean tubes and ammonium sulfate was gradually added to reach 75% saturation. After centrifugation, the supernatant was eliminated and the pellet dissolved in buffer for purification on His Trap column.

OLFM4 was purified by ammonium sulfate precipitation at 30%.

Native THBS1 purified from human platelets was purchased from Creative Biomart and used for immunization. Recombinant THBS1 protein was initially purchased from R&D Systems and later expressed and purified from cell culture supernatants of transfected HEK293 cells in house.

Antibodies

The capture and detection antibodies were mouse monoclonals generated through immunization of BALB/c mice with the recombinant proteins of human CTSD, ICAM1, OLFM4 and the native THBS1, respectively. A large number of antibodies recognizing different epitopes of the respective protein was isolated and antibody pairs were selected for subsequent development and optimization of the sandwich bead based immunoassays and the ELISA immunoassays, respectively.

The microparticle-based Luminex technology used provided a versatile platform to select antibodies for the newly developed immunoassays. The multiplexing technology facilitated the identification of antibody sandwich pairs by coupling several candidate capture antibodies to different microsphere sets. When mixed together, these sets allowed for the simultaneous testing of separate detection antibodies saving reagents, sample and time (see e.g. Baker H N, Murphy R, Lopez E, Garcia C. Conversion of a capture ELISA to a Luminex xMAP assay using a multiplex antibody screening method. J Vis Exp. 2012). Once suitable antibody pairs were selected, buffer compositions and antibody concentrations were optimized accordingly in order to yield the most optimal conditions (signal to background ratio, dilutional linearity, dynamic range of standard curve, assay sensitivity) for the individual immunoassays.

Bead Based Immunoassays

Bead-based sandwich immunoassays were established on the Luminex system as follows. Capture antibodies were covalently conjugated to carboxylated Luminex microparticles and the detection antibodies were labeled with biotin (B) according to standard procedures. 96-well half area microtiter plates (Corning Inc.) were blocked for a minimum of 15 min with 1× Blocking Reagent for ELISA (Roche Diagnostics). A mix of the capture antibody-coated microparticle and the biotinylated detection antibody at the appropriate concentrations was prepared and added to the protein (sample or standard) diluted in assay buffer within the 96-well plate. Following a 60 or 120 min incubation at 21° C. or 37° C. depending on the assay and shaking at 650 rpm in an Eppendorf ThermoMixer C, the plates were washed with PBS+0.05% Tween20 using a magnetic plate separator (Luminex Corporation). Streptavidin-phycoerythrin conjugate (Strep-PE, Moss Inc.) diluted in assay buffer was added for 30 min, incubated with 650 rpm at 21° C. in an Eppendorf ThermoMixer C. After washing, the bead conjugates were resuspended in Blocking Reagent. Read-out was performed with either a Luminex FlexMap3D or Luminex MAGPIX instrument operated with xPONENT 4.1 or 4.2 software which was also used to calculate the concentrations using 4-parameter curve fit. All samples were measured in independent duplicates on the same plate. Quality control samples with defined protein concentrations were included on each plate.

For the various epitopes of the antibodies, respective capture antibody beads and biotinylated detection antibodies were generated and tested, and the optimum pair of capture and detection antibodies was empirically determined based on optimum readout intensity (see also FIG. 1).

Enzyme-Linked Immunosorbent Assay

Sandwich ELISAs were established as follows. Capture antibodies as determined and selected using the bead-based immunoassays described in the previous chapter were diluted in 50 mM sodium phosphate buffer, pH 8.0 (alternative: 50 mM carbonate buffer, pH 9.6) and coated to 96-well Maxisorp plates (Nunc) overnight at 4° C. (alternative: at 30° C. for 75 min or at room temperature for 1 to 6 hours). After removal of the solution and wash once with PBS/0.05% Tween20, plates were blocked with BSA-block (Candor Bioscience) (alternative: PBS with 1% BSA) for 1.5 hours. Plates were then washed 3 times. The standard or serum sample were diluted in Low Cross Buffer (LCB; Candor Bioscience) (alternative: PBS-based or 10 mM Tris, 0.9% sodium chloride-based buffers, both supplemented with 1% BSA, 0.1% bovine gamma globulins, 0.1% mouse IgG) and mixed in the wells with an equal volume the biotinylated detection antibody as determined and selected using the bead-based immunoassays described in the previous chapter diluted in LCB buffer. Following a 60 min incubation at 37° C. and shaking at 650 rpm in an Eppendorf ThermoMixer C, the plates were washed 3 times with PBS/0.05% Tween20. Streptavidin-HRP conjugate (Jackson ImmuneResearch) was diluted in LCB (alternative: BSA-block diluted with an equal volume of PBS) and added for 30 min, incubating at 37° C. and shaking at 650 rpm in an Eppendorf ThermoMixer C. After washing three times with PBS/0.05% Tween20, TMB substrate (Sigma) solution (diluted in 30 mM Citric acid, pH 4.1 with $H_2O_2$) (alternative: TMB, Enhanced K-Blue TMB Substrate ready to use, Neogen) was added for 30 min, incubating at 37° C. and shaking at 650 rpm in an Eppendorf ThermoMixer C. The reaction was blocked by addition of an equal volume of 0.25 M $H_2SO_4$ (alternative: 1.0 M HCl). Absorbance was measured on FLUOStart Optima ELISA reader (BMG LabTech) reading at 450 nm and subtracting reading at 620 nm. Concentrations were calculated using 5-parameter curve fit (alternative: use 4-parameter curve fit) with the FLUOstar OPTIMA software or with Magellan from Tecan.

PSA Measurements

Serum total PSA (tPSA) and free PSA (fPSA) were analyzed using the ADVIA Centaur immunoassay system (Siemens Healthcare). Percent free PSA (% fPSA) was calculated using the measured values of tPSA and fPSA with the following formula % fPSA=fPSA/tPSA. Alternatively the total PSA (tPSA) and complexed PSA (cPSA) can be measured and the proportion of free PSA can be calculated as follows: % fPSA=(tPSA−cPSA)/tPSA. The proportion fPSA/tPSA was used for the evaluations.

Specific Bead Based Assays

For the THBS1 assay, the sample serum (at final dilution of 1:10,000) or recombinant standard was incubated with the capture antibody-coated microparticle and the biotinylated detection antibody in Low Cross Buffer (Candor Bioscience) (LCB, pH 7.2) for 60 min at 37° C. All samples were quantified in the linear range of detection of the assay and the determined concentration (CV<20% for each sample, average CV for samples on one plate of 5.1%) ranged between 14.2 and 209 µg/ml.

For the dilution of the THBS1 assay the following system was used: LCB, pH 7.2.

For the CTSD assay, the sample serum (at final dilution of 1:15) or recombinant standard was incubated with the capture antibody-coated microparticle and the biotinylated detection antibody in LCB (pH 7.2)+0.05% Tween for 120 min at 37° C. All samples were quantified in the linear range of detection of the assay and the determined concentration (CV<20% for each sample, average CV for samples on one plate of 2.8%) ranged between 40 and 453 ng/ml.

For the dilution of the CTSD assay the following system was used: LCB (pH 7.2)+0.05% Tween For the ICAM1 assay, the sample serum (at final dilution of 1:100) or recombinant standard was incubated with the capture antibody-coated microparticle and the biotinylated detection antibody in LCB (pH 7.2)+250 mM NaCl for 60 min at 37° C. All samples were quantified in the linear range of detection of the assay and the determined concentration (CV<15% for each sample, average CV for samples on one plate of 2.2%) ranged between 44 and 287 ng/ml.

For the dilution of the ICAM1 assay the following system was used: LCB (pH 7.2)+250 mM NaCl.

For the OLFM4 assay, the sample serum (at final dilution of 1:10) or recombinant standard was incubated with the capture antibody-coated microparticle and the biotinylated detection antibody in LCB (pH 7.2)+250 mM NaCl+5 mM DTT for 60 min at 37° C. All samples except three were quantified in the linear range of detection of the assay and the determined concentration (CV<15% for each sample, average CV for samples on one plate of 5.5%) ranged between 1 and 291 ng/ml.

For the dilution of the OLFM4 assay the following system was used: LCB (pH 7.2)+250 mM NaCl+5 mM DTT.

For the calibration of the concentrations to allow for quantitative readout standard solutions of the respective proteins were used using the following procedure:

Measurement of protein biomarkers means the quantification of the concentration of such biomarkers relative to an external protein standard. Namely, a reference standard curve is prepared by measuring defined concentrations of 5-7 protein standards diluted in assay buffer in the same set of measurements of the samples.

The following concentrations of the individual standards were used for the bead-based assays:

THBS1 (ng/ml): 50.00, 20.00, 8.00, 3.20, 1.28, 0.51, 0.20
CTSD (ng/ml): 75.0, 2.0, 8.33, 2.78, 0.93, 0.31, 0.10
ICAM1 (ng/ml): 12.6, 5.04, 2.02, 0.81, 0.32, 0.13, 0.05
OLFM4 (ng/ml): 120, 34.29, 9.79, 2.79, 0.80, 0.23, 0.07

The following concentrations of the individual standards were used for the ELISA assays:

THBS1 (ng/ml): 200 or 250, 100, 50 or 40, 25 or 16, 12.50 or 6.4, 6.25 or 2.6, 3.125 or 1.0
CTSD (ng/ml): 15.00, 10.00, 6.25 or 6.7, 3.91 or 4.4, 2.44 or 3.0, 1.53 or 2.0, 0.95 or 1.3

The standard curve was calculated using a computer program that allows a higher-grade polynomial curve fit. The serum samples were diluted in assay buffer so that their measurements fell within the range covered by the standards. Their concentration was calculated based on the curve of the standards, multiplying with the dilution factor to determine the concentration in the serum samples.

Specific Enzyme-Linked Immunosorbent Assays

The sample serum was measured at final dilution of 1:2,500 for the THBS1 assay and 1:20 for the CTSD assay. Also possible is measurement with 1:50 dilution for CTSD.

Results

The proposed test measures multiple cancer-specific proteins including cathepsin D (CTSD), thrombospondin 1 (THBS1) and olfactomedin 4 (OLFM4) and intercellular adhesion molecule 1 (ICAM1) individually and in various combinations in order to determine the optimum measurement strategy allowing for the highest sensitivity and specificity at the lowest measurement expenses. The test result additionally includes the % fPSA proportion (ratio of fPSA to tPSA). A combined score is calculated using the above-mentioned formula (1) resulting from a mathematical combination of % fPSA, with each of the systems CTSD, THBS1, OLFM4 and ICAM1, as well as all possible combinations of % fPSA, with a pair of the systems CTSD, THBS1, OLFM4 and ICAM1. Also % fPSA is looked at with CTSD and THBS1 and optionally OLFM4 and ICAM1. The tests were evaluated in a validation study to show its added value to established clinical parameters such as % fPSA in improving PCa diagnosis.

Objective: The objective of the study was to test which combination of the proposed protein biomarkers is able to reduce the number of negative biopsies in men with elevated tPSA (2-10 ng/ml) most efficiently and most reliably. In addition, men included in the study had negative (lack of suspicion for the presence of cancer) digital rectal examination (DRE) and enlarged prostates. This patient subgroup is considered as the most difficult to decide if a prostate biopsy should be performed, because many men have benign conditions, resulting in increased tPSA values in that range, resulting in large numbers of false positive cases. The goal of the study was to reduce the number of negative biopsies by at least 50% while having at least 90% sensitivity for PCa and a high (90-95%) negative predictive value (NPV) for high-grade PCa (Gleason score ≥7). The NPV is an important measure for the urologists indicating the probability that a negative result is truly negative.

Design, setting and participants: A retrospective study of men with a tPSA 2-10 ng/ml cancer negative DRE and enlarged prostate (volume ≥35 ml) who underwent prostate biopsy was conducted. Whole blood samples of prostate cancer-positive and negative men were collected before undergoing prostate biopsy at a leading cancer center in Northern Europe. All samples were taken between 2011-2016 following written patient consent.

Measurements: Serum tPSA and fPSA were analyzed for all samples using the ADVIA Centaur immunoassay system (Siemens Healthcare). Concentration levels of CTSD, THBS1, OLFM4 and ICAM1 were measured using the developed bead-based immunoassays as detailed above. In addition, concentration levels of CTSD and THBS1 were measured using the developed ELISA immunoassays.

Results: Of the 474 men included in this study, 236 men had a negative biopsy and 238 were diagnosed with PCa based on biopsy. Of these, 130 had low-grade (Gleason score ≤6) and 106 had high-grade PCa (Gleason score ≥7) according to prostate biopsy. Optimally correlating the measured concentration/proportion values of the samples with the actual biopsy results of the men included in this study using the above-mentioned formula for the combined score value optimizing the logistic regression formula for a maximum area under the curve was used to determine optimum sensitivity and specificity.

The ROC curves illustrated in FIGS. 2-11,13, and 15-17 are training curves, i.e. the curves obtained after optimization of the model correlating in an optimized manner the measured proportion of % fPSA, and the respective concentrations of the proteins with the true diagnosis based on the prostate biopsies.

Models for CTSD, THBS1, OLFM4 and ICAM1 Individually

In a first step, the four proteins to be analyzed were looked at individually and the optimized combined score value was determined for the respective protein alone as well as in combination with % fPSA.

FIGS. 2-5 show the optimized receiver operating characteristic (ROC) training curves depicting the accuracy of individual predictors of positive prostate biopsy and thus PCa, for the case when each protein of the group THBS1, CTSD, ICAM1 and OLFM4 is measured alone, when % fPSA is measured alone, and when the concentration of the respective protein is used together with the proportion of % fPSA for the evaluation of the combined score value.

Figure 15:
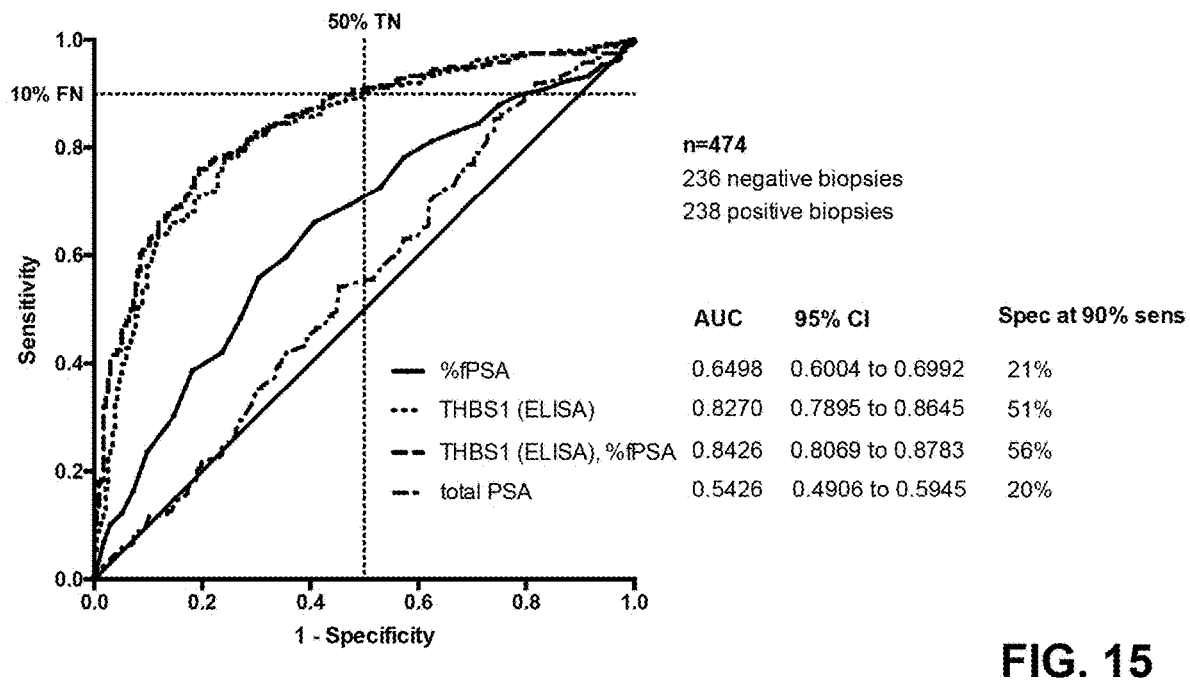
FIG. 15 shows the optimized receiver operating characteristic (ROC) training curves depicting the accuracy of individual predictors of positive prostate biopsy and thus PCa, for the case when THBS1 is measured using ELISA alone, when total PSA is measured alone, when % fPSA is measured alone, and when the concentration of THBS1 measured using ELISA is used together with the proportion of % fPSA for the evaluation of the combined score value.
Figure 16:
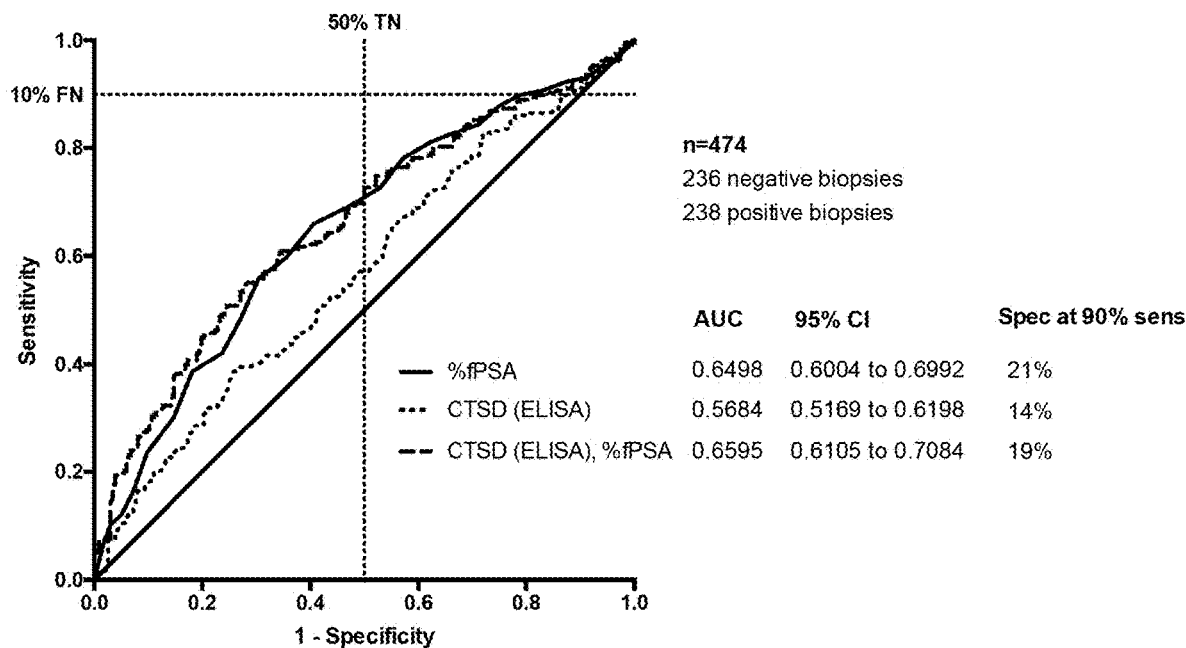
FIG. 16 shows the optimized ROC curves when CTSD is measured using ELISA alone, when % fPSA is measured alone, and when the concentration of CTSD measured using ELISA is used together with the proportion of % fPSA for the evaluation of the combined score value.
Figure 17:
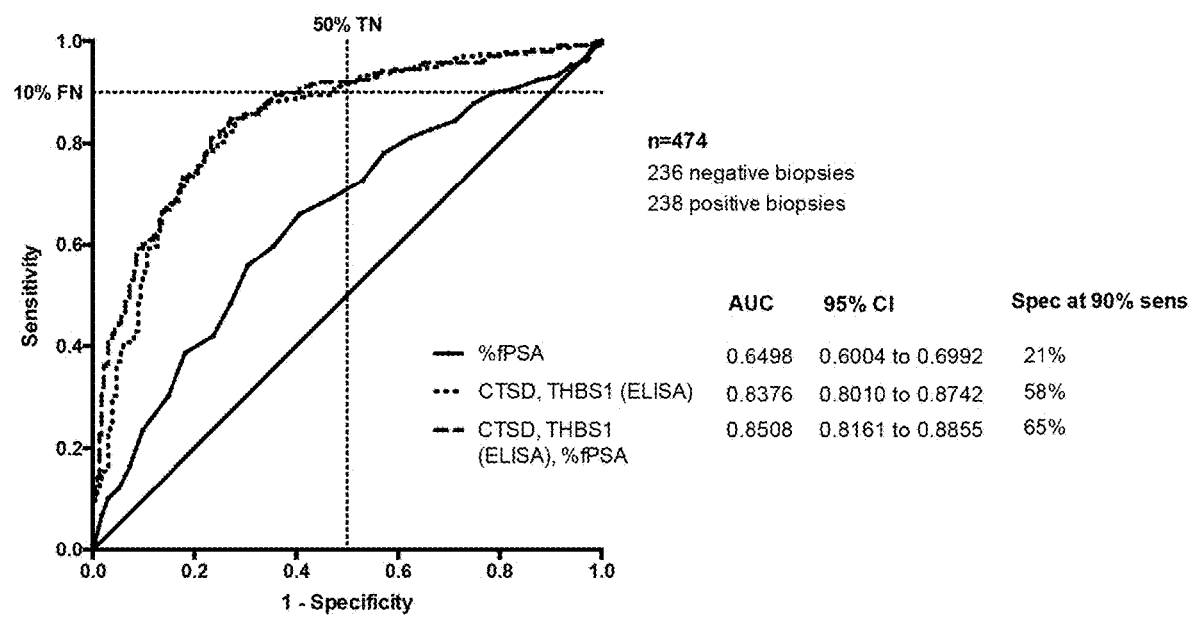
FIG. 17 shows receiver operating characteristic (ROC) training curves depicting the accuracy of individual predictors of positive prostate biopsy and thus PCa; % fPSA alone, CTSD and THBS1 both measured using ELISA, and the combination of % fPSA, CTSD and THBS1 both measured using ELISA; ROC curves of the optimized models are shown.

FIGS. 15 and 16 show the optimized ROC training curves depicting the accuracy of individual predictors of positive prostate biopsy and thus PCa, for the case when THBS1 and CTSD are measured alone using ELISA, when % fPSA is measured alone, and when the concentration of the respective protein measured by ELISA is used together with the proportion of % fPSA for the evaluation of the combined score value.

As one can see from the ROC curves, by far the best sensitivity and specificity is made available by THBS1, which so far was known to have some indicative value, but which so far has never been identified to be such a strong and reliable correlator. What one can also recognize is that CTSD, ICAM1 and OLFM4 looked at individually hardly give any benefit when comparing with % fPSA alone. In particular one notices that CTSD is essentially uncorrelated and seems to have no diagnostic value when looked at individually or in combination with % fPSA.

Total PSA concentration values are conventionally used for negative prediction of PCa because of the high sensitivity of total PSA. But as one can see from FIG. 2, the total PSA concentration values are not helpful at all for a positive prediction because of the low specificity of total PSA. As a matter of fact, only if the % fPSA value is used, reasonable AUC values can be obtained, and further only if the % fPSA values are used combined with THBS1 a high-sensitivity can be obtained. Also, if the total PSA values are evaluated in combination with THBS1, only a specificity at 90% sensitivity which is significantly below 50% is obtained and an AUC value significantly below 0.83.

Models for Pairs Selected from CTSD, THBS1, OLFM4 and ICAM1 in Combination with % fPSA In a second step, the four proteins to be analyzed were looked at in pairs and the optimized combined score value was determined for the respective protein pair alone as well as in combination with % fPSA.

FIGS. 6-11 show the optimized receiver operating characteristic (ROC) training curves depicting the accuracy of individual predictors of positive prostate biopsy and thus PCa, for the case when all possible parings of the proteins of the group THBS1, CTSD, ICAM1 and OLFM4 are measured alone, when % fPSA is measured alone, and when the concentration of the respective protein pairings is used together with the proportion of % fPSA for the evaluation of the combined score value.

Figure 3:
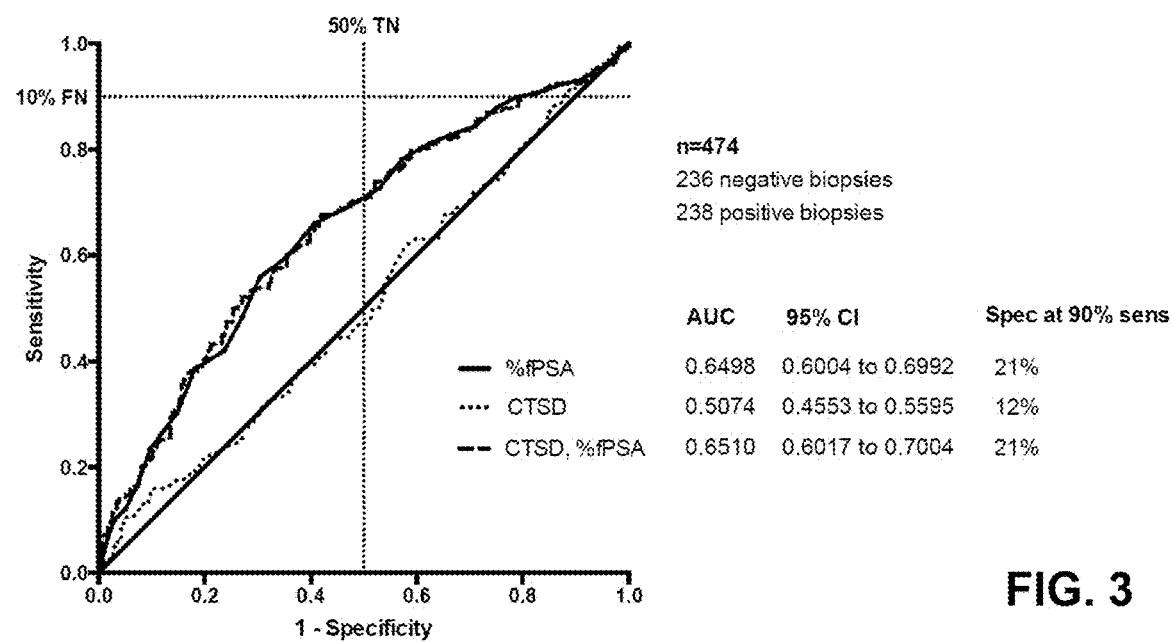
FIG. 3 shows the optimized ROC curves when CTSD is measured alone, when % fPSA is measured alone, and when the concentration of CTSD is used together with the proportion of % fPSA for the evaluation of the combined score value.
Figure 4:
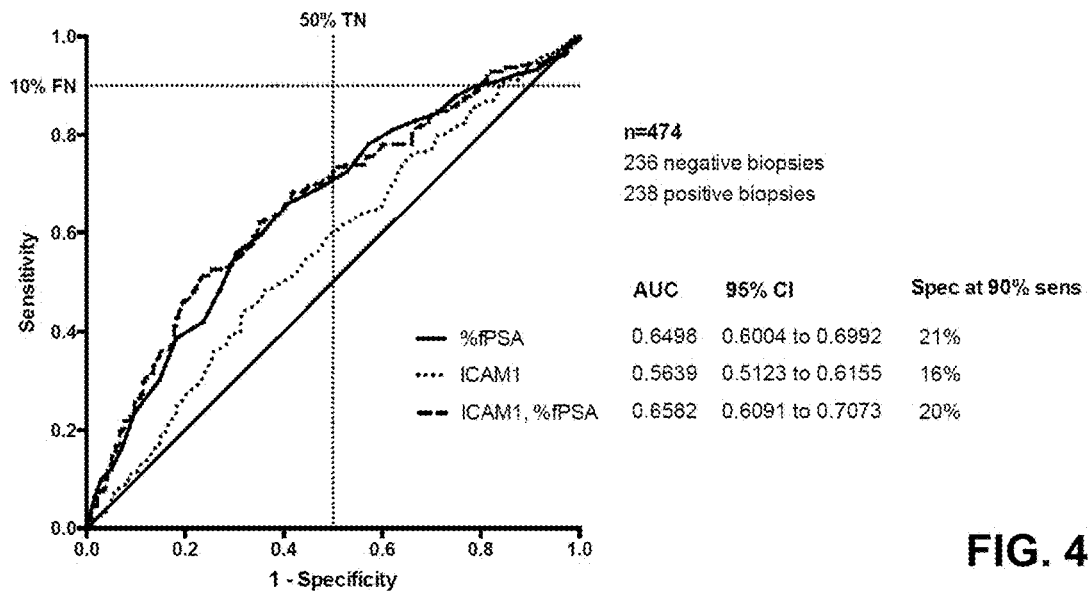
FIG. 4 shows the optimized ROC curves when ICAM1 is measured alone, when % fPSA is measured alone, and when the concentration of ICAM1 is used together with the proportion of % fPSA for the evaluation of the combined score value.
Figure 5:
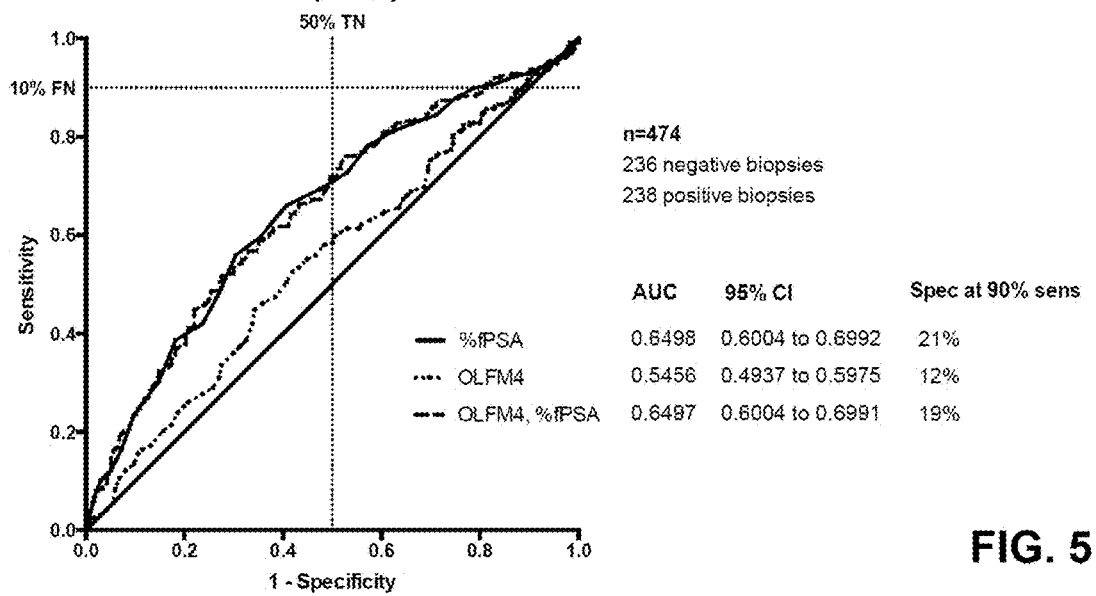
FIG. 5 shows the optimized ROC curves when OLFM4 is measured alone, when % fPSA is measured alone, and when the concentration of OLFM4 is used together with the proportion of % fPSA for the evaluation of the combined score value.

As one can see from the ROC curves, by far the best sensitivity and specificity is made available by THBS1 in combination with CTSD, which is very surprising, since CTSD alone is not giving any discrimination (see FIG. 3). This was confirmed when measuring THBS1 and CTSD using ELISA (see FIG. 17). Also THBS1 with ICAM1 and OLFM4 lead to some additional benefit, but not to the same extent as THBS1 combined with CTSD, which is completely unexpected considering the superior behavior of ICAM1 and OLFM4 taken alone (see FIGS. 4 and 5) compared with CTSD alone (see FIG. 3). There seems to be a high degree of correlation between THBS1 and CTSD levels in blood, serum and plasma hitherto unknown.

Figure 9:
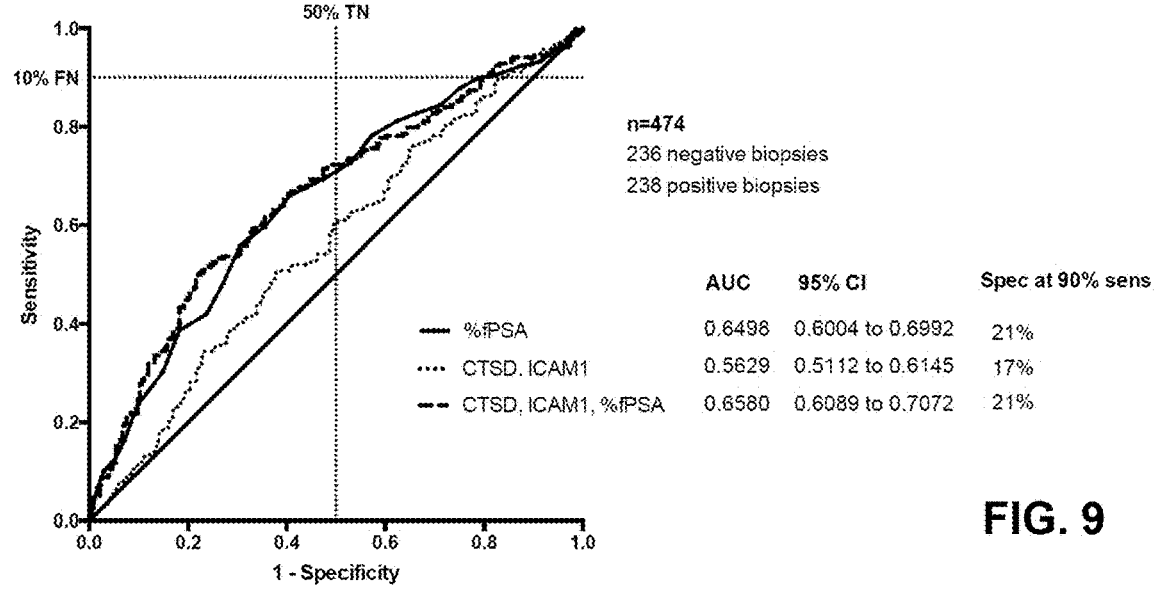
FIG. 9 shows receiver operating characteristic (ROC) training curves depicting the accuracy of individual predictors of positive prostate biopsy and thus PCa; % fPSA alone, ICAM1 and CTSD, and the combination of % fPSA, ICAM1 and CTSD; ROC curves of the optimized models are shown.
Figure 10:
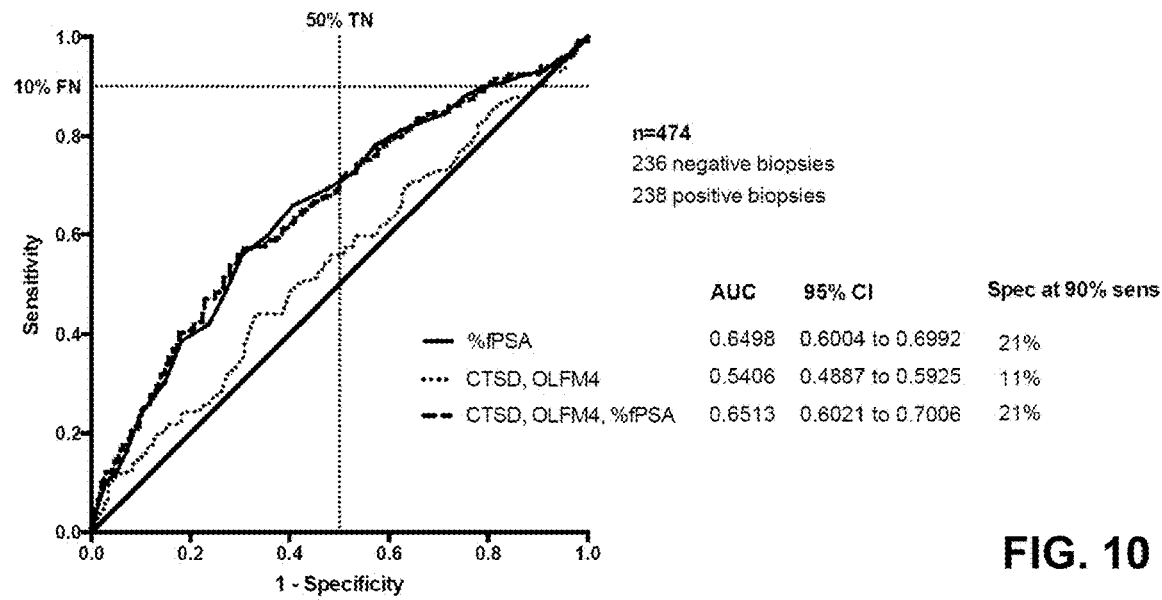
FIG. 10 shows receiver operating characteristic (ROC) training curves depicting the accuracy of individual predictors of positive prostate biopsy and thus PCa; % fPSA alone, OLFM4 and CTSD, and the combination of % fPSA, OLFM4 and CTSD; ROC curves of the optimized models are shown.
Figure 11:
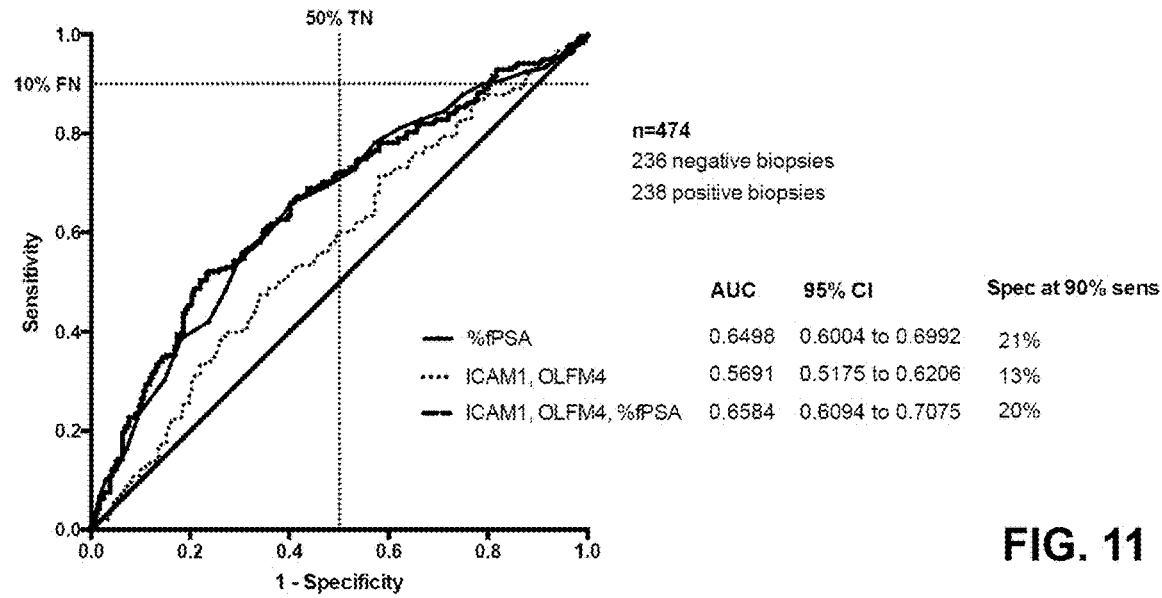
FIG. 11 shows receiver operating characteristic (ROC) training curves depicting the accuracy of individual predictors of positive prostate biopsy and thus PCa; % fPSA alone, ICAM1 and OLFM4, and the combination of % fPSA, ICAM1 and OLFM4; ROC curves of the optimized models are shown.

By contrast, the parings not involving THBS1 do not give any additional benefit, as can be seen from FIGS. 9-11. This is also unexpected, since also in these cases there could have been a high correlation leading to an additional benefit in the ROC analysis. However, no such benefit could be identified on the tested cohort.

Specific Model: % fPSA, CTSD, THBS1

Figure 6:
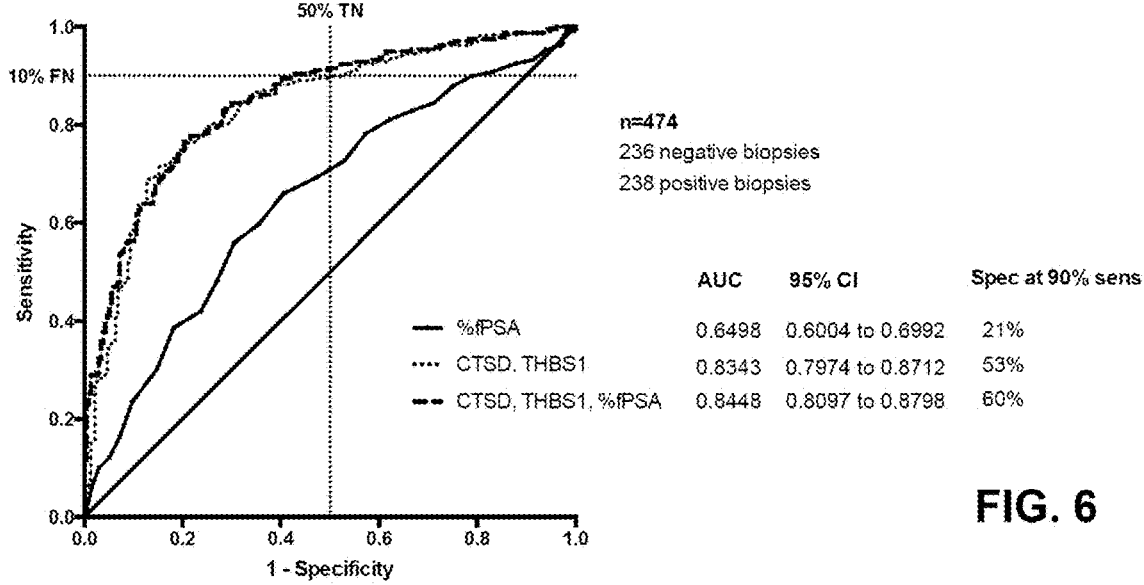
FIG. 6 shows receiver operating characteristic (ROC) training curves depicting the accuracy of individual predictors of positive prostate biopsy and thus PCa; % fPSA alone, CTSD and THBS1, and the combination of % fPSA, CTSD and THBS1; ROC curves of the optimized models are shown.
Figure 7:
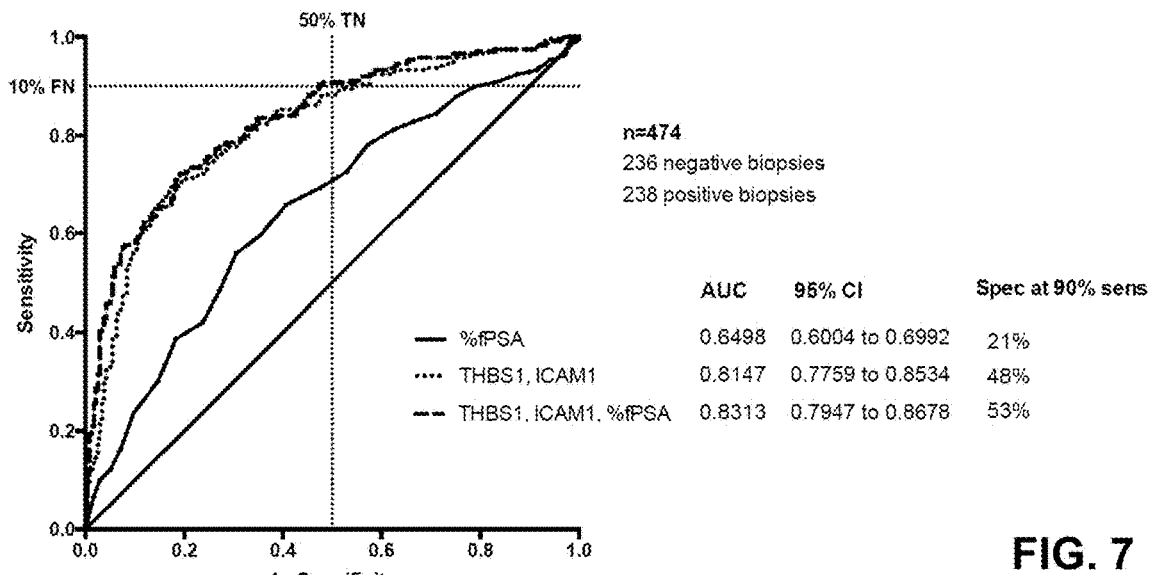
FIG. 7 shows receiver operating characteristic (ROC) training curves depicting the accuracy of individual predictors of positive prostate biopsy and thus PCa; % fPSA alone, ICAM1 and THBS1, and the combination of % fPSA, ICAM1 and THBS1; ROC curves of the optimized models are shown.
Figure 8:
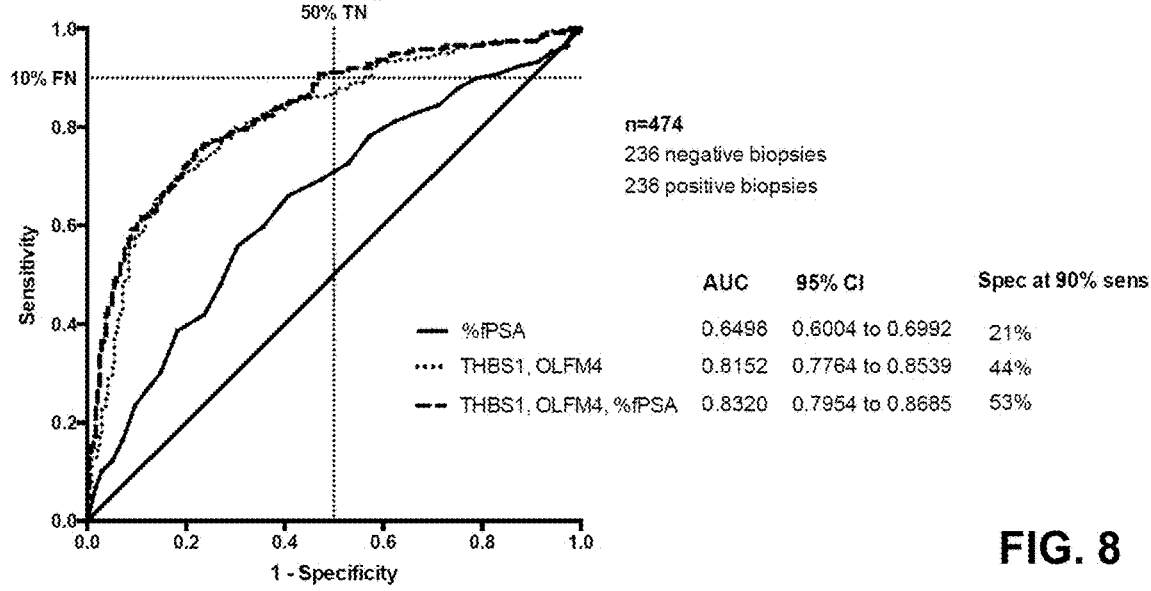
FIG. 8 shows receiver operating characteristic (ROC) training curves depicting the accuracy of individual predictors of positive prostate biopsy and thus PCa; % fPSA alone, OLFM4 and THBS1, and the combination of % fPSA, OLFM4 and THBS1; ROC curves of the optimized models are shown.
Figure 12:
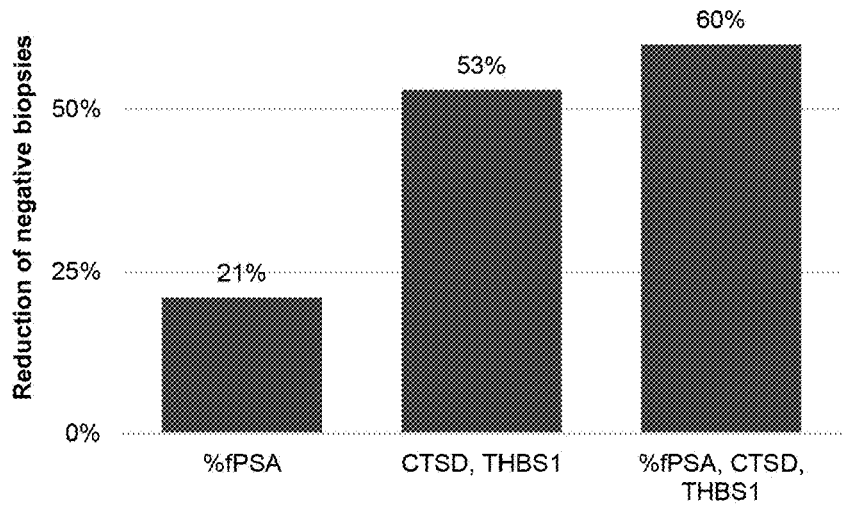
FIG. 12 shows the reduction of negative biopsies at 90% sensitivity; percentages given for % fPSA alone, CTSD and THBS1, and the combination of % fPSA, CTSD and THBS1.

FIG. 6 shows Receiver Operating Characteristic (ROC) curves for this approach. % fPSA resulted in an AUC=0.6498 (P<0.001; 95% CI=0.6004-0.6992). CTSD and THBS1 together discriminated between men with negative and positive prostate biopsies with an AUC=0.8343 (P<0.001; 95% CI=0.7974-0.8712). The combination of % fPSA, CTSD THBS1 resulted in an AUC=0.8448 (P<0.001; 95% CI=0.8097-0.8798). These results were confirmed when measuring THBS1 and CTSD using ELISA (see FIG. 17). CTSD and THBS1 together discriminated between men with negative and positive prostate biopsies with an AUC=0.8376 (P<0.001; 95% CI=0.8010-0.8742). The combination of % fPSA, CTSD THBS1 resulted in an AUC=0.8508 (P<0.001; 95% CI=0.8161-0.8855). At ≥90% sensitivity for positive prostate biopsy and thus PCa, the specificity of the combination of % fPSA, CTSD and THBS1 was 60%. In comparison, the % fPSA test commonly used in clinical practice had a specificity of 21% at the same sensitivity. This shows that CTSD and THBS1 combined with % fPSA would have avoided 141 (60%) of 236 negative biopsies and delayed the diagnosis of 10% of PCa (FIG. 12). In addition, a high NPV of 94% for high-grade PCa (Gleason score ≥7) was achieved. These results indicate that the combination of % fPSA, CTSD and THBS1 results in a significant improvement.

Figure 18:
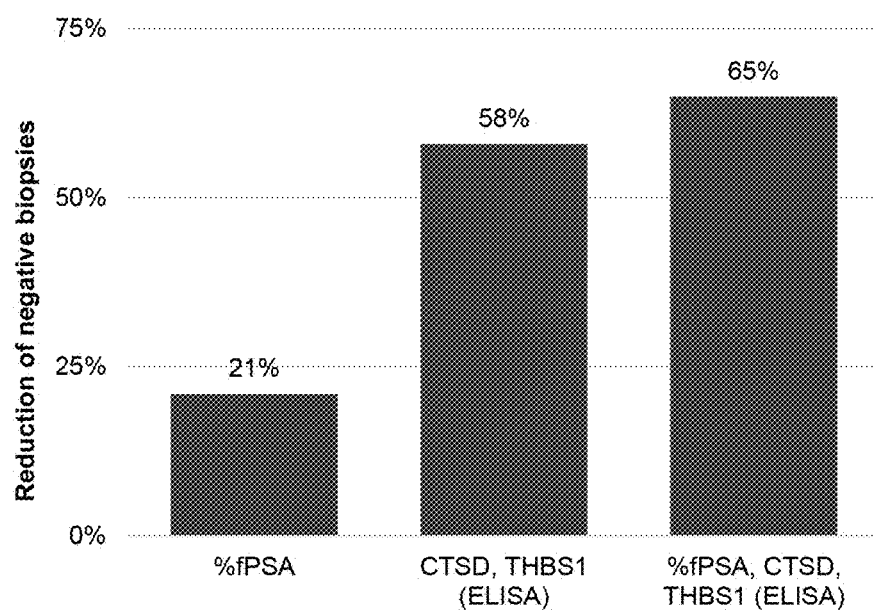
FIG. 18 shows the reduction of negative biopsies at 90% sensitivity; percentages given for % fPSA alone, CTSD and THBS1 both measured using ELISA, and the combination of % fPSA, CTSD and THBS1 both measured using ELISA.

FIG. 12 illustrates the reduction of negative biopsies at 90% sensitivity for positive prostate biopsy and thus PCa. Percentages are given for % fPSA alone, CTSD and THBS1, and the combination of % fPSA, CTSD and THBS1. These results were confirmed when measuring THBS1 and CTSD using ELISA (see FIG. 18).

In this model like in the other cases, based on the measured concentrations of % fPSA alone, CTSD and THBS1, and the combination of % fPSA, CTSD and THBS1, respectively, in each case a combined score value is calculated using the above-mentioned formula (1) with the constants obtained after optimization:

Logistic Regression Formula:

The logistic regression model used in all these results provides an estimate of the coefficients to be used in the equation (1):

$$\frac{1}{1 + e^{-(\beta_0 + \beta_1 \cdot x_1 + \ldots + \beta_k \cdot x_k)}} \quad (1)$$

Where the $\beta$s are the regression coefficients, $\beta_0$ being the intercept, and the $x_i$ are the values of the matching independent variables. The result ($p_i$) is the probability for an observation with the given pattern of values of the independent variables to have the event.

These $p_i$ are the scores that are used to build the ROC curve.

Variables in this equation for the situation of the specific Model: % fPSA, THBS1 is as follows:

| Parameter | DF | B | Standard Error | Wald Chi-Square | Pr > ChiSq | Exp(B) |
|---|---|---|---|---|---|---|
| Intercept | 1 | 4.663205 | 0.486095 | 92.029501 | 8.54E−22 | 105.975153 |
| THBS1 | 1 | −0.000053 | 0.000005 | 95.644963 | 1.37E−22 | 0.999947 |
| % fPSA | 1 | −5.381332 | 1.372877 | 15.364416 | 0.000089 | 0.004602 |

For the situation where the concentration of THBS1 as well as the % fPSA proportion is measured in the first step, for the calculation of the combined score value the regression coefficients are as follows:

$\beta_0 = 4.663$; $\beta_{THBS1} = -0.000053$; $\beta_{\% fPSA} = -5.381$.

For a 90% sensitivity a threshold value of the combined score value of larger than 0.316 is given.

Variables in this equation for the situation of the specific Model: % fPSA, THBS1, where THBS1 is measured using ELISA, is as follows:

| Parameter | DF | B | Standard Error | Wald Chi-Square | Pr > ChiSq | Exp(B) |
|---|---|---|---|---|---|---|
| Intercept | 1 | 4.902422 | 0.504822 | 94.307202 | 2.70E−22 | 134.615457 |
| THBS1 | 1 | −0.000086 | 0.000009 | 96.648592 | 8.28E−23 | 0.999914 |
| % fPSA | 1 | −5.145655 | 1.410257 | 13.313279 | 0.000264 | 0.005825 |

For the situation where the concentration of THBS1 (using ELISA) as well as the % fPSA proportion is measured in the first step, for the calculation of the combined score value the regression coefficients are as follows:

$\beta_0 = 4.902$; $\beta_{THBS1} = -0.000086$; $\beta_{\% fPSA} = -5.146$.

For a 90% sensitivity a threshold value of the combined score value of larger than 0.335 is given.

Variables in this equation for the situation of the specific Model: % fPSA, CTSD, THBS1 is as follows:

| Parameter | DF | B | Standard Error | Wald Chi-Square | Pr > ChiSq | Exp(B) |
|---|---|---|---|---|---|---|
| Intercept | 1 | 3.233 | 0.561 | 33.248 | 8.113E−9 | 25.367 |
| CTSD | 1 | 0.010 | 0.002 | 19.340 | 0.000011 | 1.010 |
| THBS1 | 1 | −0.000063 | 0.000006 | 102.843 | 3.6272E−24 | 1.000 |
| % fPSA | 1 | −4.946 | 1.393 | 12.612 | 0.00383 | 0.007 |

For a 90% sensitivity a threshold value of the combined score value of larger than 0.330 is given.

Thus, for example when the following concentrations/proportions are measured/determined in a specific sample:

| UPN | CTSD (ng/ml) | THBS1 (ng/ml) | % fPSA (0-1) |
|---|---|---|---|
| HH0106 | 227 | 78501 | 0.27 |

The following is to be evaluated:

$$p_i = \frac{1}{1+e^{-(\beta_0+\beta_1 \cdot x_{1,i}+\ldots+\beta_k \cdot x_{k,i})}} =$$

$$p_{HH0106} = \frac{1}{1+e^{-(Intercept+CTSD+THBS1+\% fPSA)}} = p_{HH0106} =$$

$$\frac{1}{1+e^{-(3.233+0.010*227-0.000063*78501-4.946*0.27)}} = p_{HH0106} = 0.31644$$

For a 90% sensitivity for positive prostate biopsy and thus PCa, the threshold of the combined score value $p_i$ is 0.330, so for the sample HH0106 no prostate biopsy would be advised since the corresponding concentration values did not indicate a positive prostate biopsy and thus the presence of PCa.

Variables in this equation for the situation of the specific Model: % fPSA, CTSD, THBS1, where CTSD and THBS1 are measured using ELISA, is as follows:

| Parameter | DF | B | Standard Error | Wald Chi-Square | Pr > ChiSq | Exp (B) |
|---|---|---|---|---|---|---|
| Intercept | 1 | 3.892 | .567 | 47.116 | 6.69E−12 | 49.022 |
| CTSD | 1 | 0.004 | 0.001 | 11.997 | .000533 | 1.004 |
| THBS1 | 1 | −0.000100 | 0.000010 | 99.352 | 2.11E−23 | 1.000 |
| % fPSA | 1 | −4.843 | 1.435 | 11.391 | .000738 | 0.008 |

For a 90% sensitivity a threshold value of the combined score value of larger than 0.362 is given.

For the situation where the concentration of THBS1, the proportion of free PSA (% fPSA), as well as the concentration of OLFM4 is measured in the first step, for the calculation of the combined score value the regression coefficients are as follows:

$\beta_0$=4.606; $\beta_{OLFM4}$=0.00271; $\beta_{THBS1}$=−0.000054; $\beta_{\% fPSA}$=−5.423.

For a 90% sensitivity a threshold value of the combined score value of larger than 0.323 is given.

For the situation where the concentration of THBS1, the proportion of free PSA (% fPSA), as well as the concentration of ICAM1 is measured in the first step, for the calculation of the combined score value the regression coefficients are as follows:

$\beta_0$=4.769; $\beta_{ICAM1}$=−0.00084; $\beta_{THBS1}$=−0.000053; $\beta_{\% fPSA}$=−5.395.

For a 90% sensitivity a threshold value of the combined score value of larger than 0.318 is given.

Model: % fPSA, CTSD, THBS1, OLFM4, ICAM1

Figure 13:
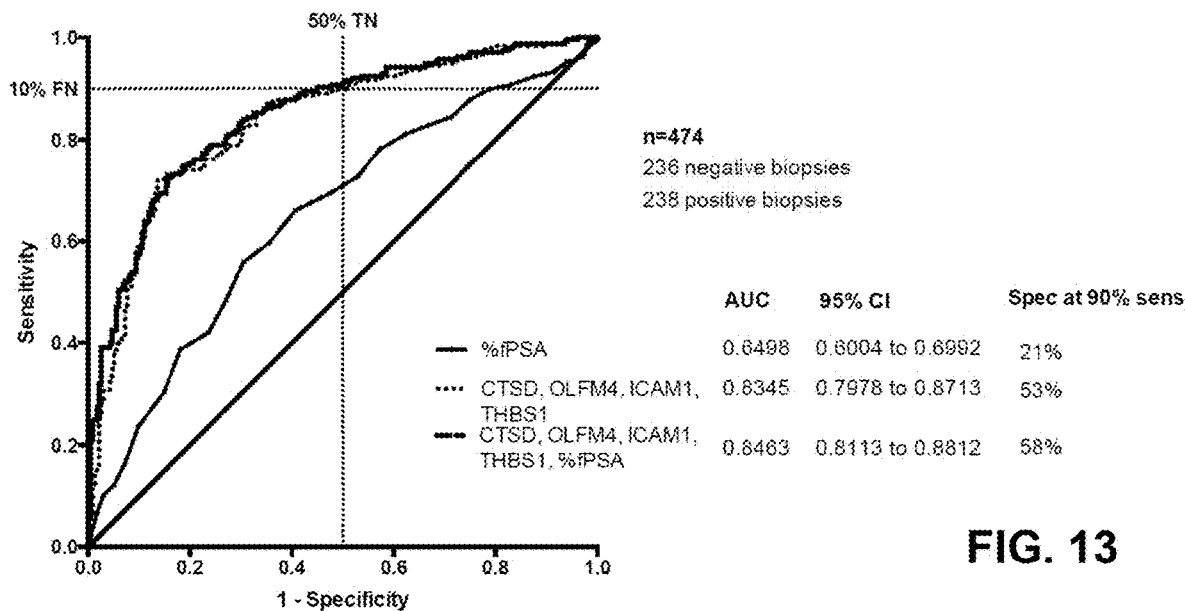
FIG. 13 shows receiver operating characteristic (ROC) training curves depicting the accuracy of individual predictors of positive prostate biopsy and thus PCa; % fPSA alone, CTSD, THBS1, OLFM4, ICAM1, and the combination of % fPSA, CTSD, THBS1, OLFM4 and ICAM1 ROC curves of the optimized models are shown.

FIG. 13 shows Receiver Operating Characteristic (ROC) curves for this approach. % fPSA resulted in an AUC=0.6498 (P<0.001; 95% CI=0.6004-0.6992). CTSD, THBS1, OLFM4 and ICAM1 together discriminated between men with negative and positive prostate biopsies with an AUC=0.8345 (P<0.001; 95% CI=0.7978-0.8713). The combination of % fPSA, CTSD, THBS1, OLFM4 and ICAM1 resulted in an AUC=0.8463 (P<0.001; 95% CI=0.8122-0.8817).

FIG. 13 shows receiver operating characteristic (ROC) curves depicting the accuracy of individual predictors of positive prostate biopsy and thus PCa. % fPSA alone, CTSD, THBS1, OLFM4, ICAM1, and the combination of % fPSA, CTSD, THBS1, OLFM4 and ICAM1 ROC curves are shown.

At ≥90% sensitivity for positive prostate biopsy and thus PCa, the specificity of the combination of % fPSA, CTSD, THBS1, OLFM4 and ICAM1 was 58%. In comparison, the % fPSA test commonly used in clinical practice had a specificity of 21% at the same sensitivity. This shows that the proposed set of markers combined with % fPSA would have avoided 136 (58%) of 236 negative biopsies and delayed the diagnosis of 10% of PCa (FIG. 13). In addition, a high NPV of 93% for high-grade PCa (Gleason score ≥7) was achieved. These results indicate that the combination of % fPSA, CTSD, THBS1, OLFM4 and ICAM1 results in a significant improvement over % fPSA alone, but no significant further improvement over % fPSA, CTSD, THBS1.

Figure 14:
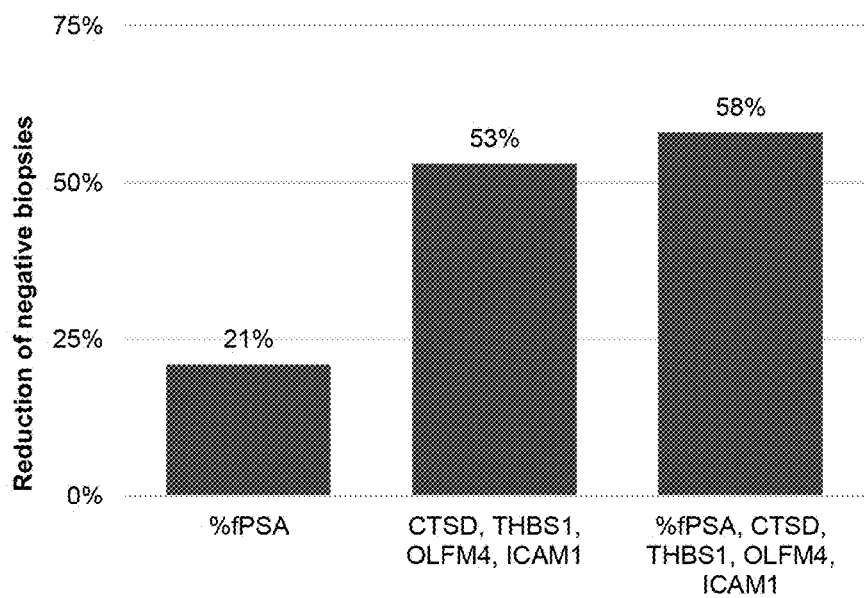
FIG. 14 shows the reduction of negative biopsies at 90% sensitivity; percentages given for % fPSA alone, CTSD, THBS1, OLFM4 and ICAM1, and the combination of % fPSA, CTSD, THBS1, OLFM4 and ICAM1.

FIG. 14 shows the reduction of negative biopsies at 90% sensitivity. Percentages given for % fPSA, CTSD, THBS1, OLFM4 and ICAM1, and the combination of % fPSA, CTSD, THBS1, OLFM4 and ICAM1.

Also here, the ROC curves illustrated in FIG. 13 are training curves, i.e. the curves obtained after optimization of the model correlating in an optimized manner the measured concentrations with the true diagnosis based on the biopsies.

Also in this model, based on the measured concentrations of % fPSA alone, CTSD, THBS1, OLFM4 and ICAM1, and the combination of % fPSA, CTSD, THBS1, OLFM4 and ICAM1, respectively, in each case a discriminator is calculated using the following formula with the constants obtained after optimization:

$\beta_0$=3.567; $\beta_{OLFM4}$=0.002; $\beta_{THBS1}$=−0.000063; $\beta_{CTSD}$=0.01; $\beta_{ICAM1}$=−0.003; $\beta_{\% fPSA}$=−5.033.

For a 90% sensitivity a threshold value of the combined score value of larger than 0.329 is given.

In terms of the formulae for p this means the following:

$$p_i = \frac{1}{1+e^{-\left(3.567+0.01[CTSD]-0.000063[THBS1]+0.002[OLFM4]-0.003[ICAM1]-5.033*\left(\frac{fPSA}{tPSA}\right)\right)}} \quad (1)$$

cut-off $p_{i=90\% sensitivity}$ = 0.329 (>0.329 = positive).

Conclusions:

Unexpectedly, the combination of THBS1 and % fPSA, and even more so the combination of CTSD, THBS1 and % fPSA is significantly more accurate than tPSA or % fPSA alone in determining the absence of PCa in men with elevated tPSA (2-10 ng/ml), enlarged prostate (≥35 ml) and negative DRE. The implementation of a test comprising these three parameters in clinical practice has the potential to significantly lower the rate of unnecessary biopsies by up to 60%.

The invention claimed is:

1. A method comprising quantitative measurement in serum, plasma, or blood of a concentration of THBS1 and CTSD in a subject, as well as a proportion of free PSA (% fPSA), wherein for the measurement of the concentration of THBS1 and CTSD, the subject's serum, plasma, or blood is diluted using a buffer having a pH value in a range of 7-7.4 and comprising an agent controlling the pH value selected from at least one of the following systems: Tris (Tris(hydroxymethyl)-aminomethane), Pipes (Piperazine-1,4-bis-2-ethane sulfonic acid), Mes (4-Morpholino ethane sulfonic acid), Hepes (4-(2-hydroxyethyl)-1-piperazine-ethane sulfonic acid), phosphate buffered saline (PBS), and wherein the buffer has an ionic strength in a range of 50-850 mM, wherein the method includes a first step being performed by contacting the subject's serum, plasma, or blood, with at least one affinity reagent for each protein and detecting whether binding occurs between the respective protein and the at least one affinity reagent and using quantitative readout of the respective protein's concentration, allowing a calculation of the respective concentration in the original serum, plasma, or blood, or in case of free PSA its proportion, wherein either a sandwich enzyme linked immunosorbent assay specific to the respective protein is used, or a sandwich bead based antibody assay to the respective protein is used, and wherein in said sandwich enzyme linked immunosorbent assay or said sandwich bead based antibody assay, mouse monoclonal antibodies that bind the respective protein are used, said mouse monoclonal antibodies having been generated through immunization of mice with the respective recombinant human THBS1 or CTSD protein;

a second step of calculating, based on all the protein concentrations as well as the free PSA proportion determined in the first step, a combined score value, further taking account of an age of the subject, a third step of determining a risk of a positive biopsy and/or prostate cancer of the subject to discriminate between benign and malignant prostatic conditions based on the combined score value as determined in the second step, wherein surpassing a corresponding threshold value of the combined score value is taken as positive prostate cancer information and/or as necessity of biopsy, wherein said combined score value is calculated using the following formula (1):

$$\text{Combined Score} = \frac{1}{1+e^{-(\beta_0+\beta_1 \cdot x_1+\ldots+\beta_k \cdot x_k)}} \quad (1)$$

wherein, in the formula (1), $\beta_i$ are regression coefficients as determined before with an optimization using experimental data, $\beta_0$ being an intercept, and wherein $x_i$ is the measured concentration of the respective protein in the original serum, plasma, or blood and in case of free PSA (% fPSA) the proportion in the original serum, plasma, or blood, wherein, for the calculation of the combined score value, the regression coefficients are chosen as follows:

$\beta_0$ in the range of 3-3.8;

$\beta_{CTSD}$ in the range of 0.005-0.05;

$\beta_{THBS1}$ in the range of $(-0.00009)$-$(-0.00003)$;

$\beta_{\%\ fPSA}$ in the range of $(-7.5)$-$(-2.5)$ wherein the concentration of THBS1, expressed in ng/ml, the proportion, expressed in the numerical range of 0-1, of free PSA (% fPSA), as well as the concentration of CTSD, in each case expressed in ng/ml, are measured in the first step, and wherein, for a 90% sensitivity, a threshold value of a combined score value is 0.3-0.35.

2. The method according to claim 1, involving the quantitative detection, in serum, plasma or blood of the subject, of the concentration of TEMS1 and CTSD, the proportion of free PSA (% fPSA), as well as the concentration of OLFM4, and ICAM1.

3. The method according to claim 2,
wherein the concentration of THBS1, expressed in ng/ml, the proportion, expressed in the numerical range of 0-1, of free PSA (% fPSA), as well as the concentration of OLFM4, ICAM1 as well as CTSD, in each case expressed in ng/ml, are measured in the first step, and wherein, for a 90% sensitivity, a threshold value of a combined score value is 0.3-0.35.

4. The method according to claim 2,
wherein for the dilution to measure THBS1 a dilution factor in the range of 1:1,000-1:20,000 is chosen for an enzyme linked immunosorbent assay and in the range of 1:5,000-1:15,000 for a bead-based assay, and/or wherein for the dilution to measure the protein CTSD a dilution factor in the range of 1:5-1:70 is chosen, for an enzyme linked immunosorbent assay and in the range of 1:10-1:20 for a bead-based assay is chosen, wherein for the dilution to measure ICAM1 a dilution factor in the range of 1:50-1:200 is chosen or wherein for the dilution to measure OLFM4 a dilution factor in the range of 1:5-1:30 is chosen.

5. The method according to claim 2, wherein at least one of OLFM4 and ICAM1 as measured comprises at least one post-translational modification selected from the group consisting of glycosylation, phosphorylation, and lipidation.

6. The method according to claim 1, wherein at least one of THBS1 and CTSD as measured comprises at least one post-translational modification selected from the group consisting of glycosylation, phosphorylation, and lipidation.

7. The method according to claim 1,
wherein for the dilution to measure THBS1 a dilution factor in the range of 1:1,000-1:20,000 is chosen for an enzyme linked immunosorbent assay and in the range of 1:5,000-1:15,000 for a bead-based assay, and/or wherein for the dilution to measure the protein CTSD a dilution factor in the range of 1:5-1:70 is chosen, for an enzyme linked immunosorbent assay and in the range of 1:10-1:20 for a bead-based assay is chosen.

8. The method according to claim 1, wherein the quantitative detection of the respective concentration involves the determination of the concentration of such biomarkers relative to an external protein standard, involving the preparation of a reference standard curve by measuring defined concentrations of several protein standards diluted in the same buffer as for the protein dilution to be measured in the same set of measurements of the samples.

9. The method according to claim 1, further comprising at least one of monitoring, diagnosis, predicting prostate biopsy outcome, prognosis, risk assessment, therapy selection, therapy monitoring of cancer.

10. The method according to claim 1,
wherein the concentration of THBS1, expressed in ng/ml, as well as the proportion, expressed in the numerical range of 0-1, of free PSA (% fPSA), and further the concentration of CTSD, expressed in ng/ml, is measured in the first step, and
wherein for the calculation of the combined score value in of measuring THBS1, the proportion of free PSA (% fPSA) as well as CTSD, the regression coefficients are chosen as follows:
$\beta_0$ in the range of 3.1-3.3;
$\beta_{CTSD}$ in the range of 0.008-0.012;
$\beta_{THBS1}$ in the range of $(-0.00007)$-$(-0.00006)$;
$\beta_{\% fPSA}$ in the range of $(-5.2)$-$(-2.5)$.

11. The method according to claim 1,
wherein the concentration of THBS1, expressed in ng/ml, as well as the proportion, expressed in the numerical range of 0-1, of free PSA (% fPSA), and further the concentration of CTSD, expressed in ng/ml, is measured in the first step, and
wherein, for the calculation of the combined score value of measuring THBS1, the proportion of free PSA (% fPSA) as well as CTSD, the regression coefficients are chosen as follows:
$\beta_0$ in the range of 3.1-3.3;
$\beta_{CTSD}$ in the range of 0.008-0.012;
$\beta_{THBS1}$ in the range of $(-0.00007)$-$(-0.00006)$;
$\beta_{\% fPSA}$ in the range of $(-5.2)$-$(-2.5)$, and
wherein for a 90% sensitivity a threshold value of the combined score value of 0.33-0.34 is selected.

12. The method according to claim 2,
wherein the concentration of THBS1, expressed in ng/ml, the proportion, expressed in the numerical range of 0-1, of free PSA (% fPSA), as well as the concentration of OLFM4, ICAM1 as well as CTSD, in each case expressed in ng/ml, are measured in the first step, and
wherein, for the calculation of the combined score value, the regression coefficients are chosen as follows:
$\beta_0$ in the range of 3-3.8;
$\beta_{OLFM4}$ in the range of 0.001-0.003;
$\beta_{ICAM1}$ in the range of $(-0.004)$-$(-0.002)$;
$\beta_{CTSD}$ in the range of 0.005-0.05;
$\beta_{THBS1}$ in the range of $(-0.00009)$-$(-0.00003)$;
$\beta_{\% fPSA}$ in the range of $(-7.5)$-$(-2.5)$
and wherein for a 90% sensitivity a threshold value of the combined score value of 0.3-0.35 is selected.

13. The method according to claim 2,
wherein the concentration of THBS1, expressed in ng/ml, the proportion, expressed in the numerical range of 0-1, of free PSA (% fPSA), as well as the concentration of OLFM4, ICAM1 as well as CTSD, in each case expressed in ng/ml, are measured in the first step, and
wherein for the calculation of the combined score value the regression coefficients are chosen as follows:
$\beta_0$ in the range of 3.5-3.6;
$\beta_{OLFM4}$ in the range of 0.0015-0.0025;
$\beta_{ICAM1}$ in the range of $(-0.0035)$-$(-0.00025)$;
$\beta_{CTSD}$ in the range of 0.008-0.012;
$\beta_{THBS1}$ in the range of $(-0.00007)$-$(-0.00006)$;
$\beta_{\% fPSA}$ in the range of $(-5.2)$-$(-4.8)$, and
wherein for a 90% sensitivity a threshold value of the combined score value of 0.32-0.335 is selected.

14. The method according to claim 2,
wherein for the measurement of the concentration of at least one of THBS1, CTSD, OLFM4, and ICAM1, the subject's serum, plasma or blood is diluted using a buffer having a pH value in the range of 7-7.4 and comprising an agent controlling the pH value, with additional components selected from at least one system as follows: non-ionic detergent, in a concentration of 0.01 to 0.1% (v/v), and selected from at least one of the group consisting of: Dodecylpoly(ethyleneglycolether)m, wherein m is an integer of 5 to 40; 1-O-n-Octyl-β-D-glucopyranoside (n-Octylglucoside); Alkylphenolpoly(ethyleneglycol-ether)m, wherein m is an integer of 5 to 40; 1-O-n-Dodecyl-β-D-glucopyranosyl (1-4)alpha-D-glucopyranoside; Dodecylpoly-(ethyleneglycolether)m, wherein m is an integer of 5 to 40; Poly(oxyethylene)(20)-sorbitane mono fatty acid ester; Octylphenolpoly(ethyleneglycoiether)m, wherein m is an integer of 5 to 40; bovine serum albumin; mouse IgG; bovine gamma globulins; fetal bovine serum; horse serum.

15. The method according to claim 2,
wherein for the measurement of the concentration of at least one of THBS1, CTSD, OLFM4, and ICAM1, the subject's serum, plasma or blood is diluted using a buffer having a pH value in the range of 7-7.4 and comprising an agent controlling the pH value, selected from at least one of the following systems: Tris (Tris (hydroxymethyl)-aminomethane), Pipes (Piperazine-1, 4-bis-2-ethane sulfonic acid), Mes (4-Morpholino ethane sulfonic acid), Hepes (4-(2-hydroxyethyl)-1-piperazine-ethane sulfonic acid), phosphate buffered saline (PBS), with or without additional components selected from at least one system as follows: non-ionic detergent, in a concentration of 0.025-0.05% (v/v), and selected from at least one the group consisting of: Dodecylpoly(ethyleneglycolether)m, wherein m is an integer of 5 to 40; 1-O-n-Octyl-β-D-glucopyranoside (n-Octylglucoside); Alkylphenolpoly(ethyleneglycolether)m, wherein m=11; 1-O-n-Dodecyl-β-D-glucopyranosyl (1-4)alpha-D-glucopyranoside; Dodecylpoly-(ethyleneglycolether)m, wherein m=23; Poly(oxyethylene)(20)-sorbitane mono fatty acid ester, selected from Poly(oxyethylene)(20)-sorbitane monooleate, Poly(oxyethylene)(20)-sorbitane monolaurate, Poly(oxyethylene)(20)-sorbitane monopalmitat, Poly(oxyethylene)(20)-sorbitane monostearate); Octylphenolpoly(ethyleneglycoiether)m, wherein m=10; bovine serum albumin; mouse IgG; bovine gamma globulins; fetal bovine serum; horse serum;
wherein the buffer has a ionic strength in the range of 250-370 mM.

16. The method according to claim 2,
wherein, for the dilution to measure THBS1, a dilution factor is in the range of 1:2,000-1:3,000 for an enzyme linked immunosorbent assay and in the range of 1:5,000-1:15,000 for a bead-based assay, or
wherein, for the dilution to measure the protein CTSD, a dilution factor is in the range of 1:10-1:30 for an enzyme linked immunosorbent assay and in the range of 1:10-1:20 for a bead-based assay, and
wherein the buffer used is further supplemented with a non-ionic detergent selected as Poly(oxyethylene)(20)-sorbitane monolaurate to lead to an additional concentration thereof of 0.05% (v/v), or
wherein, for the dilution to measure ICAM1, a dilution factor is in the range of 1:80-1:150, and
wherein the buffer used is further supplemented with sodium chloride to an additional sodium chloride content of 250 mM, or wherein, for the dilution to measure OLFM4, a dilution factor is in the range of 1:5-1:20, and wherein the buffer used is further supplemented with sodium chloride to an additional sodium chloride content of 250 mM as well as a reduction agent, selected as dithiothreitol to lead to a concentration of 5 mM thereof.

17. The method according to claim 1, wherein the method includes:

a first step being performed by contacting the subject's serum, plasma or blood, after dilution thereof, with at least one affinity reagent for each protein and detecting whether binding occurs between the respective protein and the at least one affinity reagent and using quantitative readout of the respective protein's concentration or in case of free PSA its proportion, allowing the calculation of the respective concentration in the original serum, plasma or blood, and wherein in this first step either a sandwich enzyme linked immunosorbent assay specific to the respective protein with visible readout is used, or a sandwich bead based antibody assay to the respective protein with fluorescent readout is used.

18. The method according to claim 1, wherein the quantitative detection of the respective concentration involves the determination of the concentration of such biomarkers relative to an external protein standard, involving the preparation of a reference standard curve by measuring defined concentrations of 5-7 protein standards diluted in the same buffer as for the protein dilution to be measured in the same set of measurements of the samples.

19. The method according to claim 1, further including at least one of monitoring, diagnosis, predicting prostate biopsy outcome, prognosis, risk assessment, therapy selection, therapy monitoring of localized or non-localized prostate cancer.

\* \* \* \* \*